(12) United States Patent
Albertsen et al.

(10) Patent No.: US 12,133,495 B2
(45) Date of Patent: Nov. 5, 2024

(54) METHODS AND COMPOSITIONS FOR PRODUCING CLONAL, NON-REDUCED, NON-RECOMBINED GAMETES

(71) Applicants: PIONEER HI-BRED INTERNATIONAL, INC., Johnston, IA (US); E.I. DU PONT DE NEMOURS AND COMPANY, Wilmington, DE (US)

(72) Inventors: Marc C Albertsen, Grimes, IA (US); Tim Wayne Fox, Des Moines, IA (US); Marissa Simon, Grimes, IA (US); Mark E Williams, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 327 days.

(21) Appl. No.: 16/085,838

(22) PCT Filed: Mar. 17, 2017

(86) PCT No.: PCT/US2017/022962
§ 371 (c)(1),
(2) Date: Sep. 17, 2018

(87) PCT Pub. No.: WO2017/161264
PCT Pub. Date: Sep. 21, 2017

(65) Prior Publication Data
US 2019/0098858 A1   Apr. 4, 2019

Related U.S. Application Data

(60) Provisional application No. 62/310,006, filed on Mar. 18, 2016.

(51) Int. Cl.
*A01H 6/46* (2018.01)
*C07K 14/415* (2006.01)
*C12N 15/82* (2006.01)

(52) U.S. Cl.
CPC ......... *A01H 6/4684* (2018.05); *C07K 14/415* (2013.01); *C12N 15/8287* (2013.01)

(58) Field of Classification Search
None
See application file for complete search history.

(56) References Cited

U.S. PATENT DOCUMENTS

| | | | | |
|---|---|---|---|---|
| 6,630,614 | B1 * | 10/2003 | Mahajan | C07K 14/415 |
| | | | | 435/320.1 |
| 2012/0266324 | A1 * | 10/2012 | Lawit | C12N 15/8218 |
| | | | | 800/275 |
| 2014/0298507 | A1 * | 10/2014 | Chan | A01H 4/005 |
| | | | | 800/298 |

FOREIGN PATENT DOCUMENTS

| | | |
|---|---|---|
| EP | 2208790 A1 | 7/2010 |
| WO | 2012075195 A1 | 6/2012 |

OTHER PUBLICATIONS

Zhu, Efficiency and Inheritance of Targeted Mutagenesis in Maize Using CRISPR-Cas9, Journal of Genetics and Genomics 42 (2016) 25-36, Published Dec. 21, 2015 (Year: 2015).*
Singh, Production of Viable Gametes without Meiosis in Maize Deficient for an ARGONAUTE Protein, The Plant Cell, Feb. 2011 (Year: 2011).*
Barcaccia, Apomixis in plant reproduction: a novel perspective on an old dilemma, Plant Reproduction, 2013, Issue 26, pp. 159-179 (Year: 2013).*
Sidhu, Evolution of meiotic recombination genes in maize and teosinte, BMC Genomics, 2017, 18: 106 (Year: 2017).*
Cromer, L. et al. "OSD1 Promotes Meiotic Progression via APC/C Inhibition and Forms a Regulatory Network with TDM and CYCA1;2/TAM", Jul. 1, 2012, PLOS Genetics, vol. 8, No. 7, p. E1002865-2.
D'erfurth, I et al. "Turning Meiosis into Mitosis Academic Editor", PLos Biol, Jan. 1, 2009, https://doi.org/10.1371/journal.pbio.1000124.
International Search Report and Written Opionion, International Application No. PCT/US2017/022962 mailed Jun. 6, 2017.
International Preliminary Report on Patentability for International Application No. PCT/US2017/022962, mailed Sep. 27, 2018, 7 Pages.

* cited by examiner

*Primary Examiner* — Weihua Fan
*Assistant Examiner* — Brian James Sullivan

(57) ABSTRACT

Methods and compositions useful for avoiding plant meiosis and clonal reproduction through seed are provided herein. The present disclosure provides polynucleotides and related polypeptides of Spo11, Rec8, OSD1-1A, and OSD1-3A and methods and compositions for suppressing their expression level or activity.

20 Claims, No Drawings

Specification includes a Sequence Listing.

SEQUENCE LISTING

```
<160> NUMBER OF SEQ ID NOS: 22

<210> SEQ ID NO 1
<211> LENGTH: 3104
<212> TYPE: DNA
<213> ORGANISM: Zea mays

<400> SEQUENCE: 1
```

```
caacaaggac agagcagaaa cttagccaga gattcgtcca ggatagggc tgtatcgtag      60 ggagtagtcg ttgcggagat tgggtcgaag cggactggac aggagccgag caaactgtga     120
gtattgtatt ttctcttttg cggtttggag ggtttggatg tggttgtttg gttgcagttt    180
tccgagcgtt ttagtgatgt ggttttcct cttgccatgt cctttcagat ctgcagaaga     240
ggttaaaggg ttgccgtgcg gactccggag ctgtgagaat ctaccccgag gtgagaatct    300
ctaaacggtt gtggccttga gggatgcggt tagttcttgg tccgattatg ttagttcgcc    360
cccgaattgc tttcttcaga cgtgtttcgt ggcttcttta tgtgtaaatc ccttggaggg    420
tagagcattg aggcggggtt atgagtagaa ccgtcgcaga ttaaatgatt atgaccgtgt    480
ttctttacgc aatttcttcg tgctattggt acttatacac tgctctcctc tgcgttgcgt    540
ctttcttgca ggtaagctct tagagtcgta gtcaaagagg agaagccagg ccgggaacaa    600
acagaaaagt gaggagattt gttggtgcat tagctactca cgcgtcccct gaaattctgc    660
ttgttaactc catcctaaaa tttattgtgt ggacccagga gaagagcaac aggagtacag    720
gactcagtgc accaagaata ggaaagagca agaccataa cagttgtatg agatactgtg     780
atttctgggt tcatttgttt atctgattat gcgttctttg gtctcttgca tcactcatgt    840
ggttgtatgc actcctccag gaacttcaag atgcttgaag tgaggactgc aagaaggccg    900
gctctcgccg acatctctgg tggtgggttc tttatgagga cagtagaatc gccaggagct    960
gtgctggtga atggtgctgt caagcggccg gctcggcagt ttctatcacc ttcaagcaac   1020
aaggagaatg tgccaccagt gggagctttc agggctacac caagaggag accccttg     1080 cctgactggt acccgaggac accactccgt gacatcacat caatcgtcaa ggtggtggac   1140
tatttccttg ctattgtcta attccatttt gttgtatttg gtgcatgcac tgtactctat   1200
aatatgctac agtgtggtgc aatgtttcat ttgtgagtcc ttgtgttcag aatgcctggt   1260
tagtggccaa caaagatagg ttatgtagta ggtttggtaa ttggtattca gaatgttgag   1320
ccttgtacac tattattcta taatacaata gatctgccag ttctgctagc tgccttgatg   1380
acatagaatg agaaatatat acagttggat tttatcatta gtttagcaac tcatagcaaa   1440
agattcttat aatttcaaat aacatagtaa taatactctt acaagacatt accaacactc   1500
ttttattcta tcttacttgc atctagctgt gttcactatt cagttttagg tgcctgacca   1560
tttaaatgtg cttaaatttg cagaaaggtc agtagtcaat aaggcatgtt aaatctaaat   1620
ttattcttct ccattgtact taatgttacc ccatttcccc ttattctctt tattctcttt    1680
gaatatttaa ccgatcataa tagatgttcc tttgtgtcgt gactgaatta ctgtacttgt   1740
ttgtagaaac tacgcactgc aactaaaaag tcacacactt taggctgtca tgttaagaag    1800
ttatatacag gattgtgttt agaaattcat tgacaatttg ccatgatccg taaacttaag   1860
tcagttgttg aggatcttat ttgcaacggc atgtcttctt agttgttctg aaatgtccat   1920
tcatttaaac gtagcctact aaaaatgaga ttcctataaa gattcatagt atagggtttc   1980
gacttcatct ttagttttaa gctttatatg accaatctat ttaggatatt tgcaagaatg   2040
tcatttggtg ttttttaatga ttttaatcgt cttcataact tatattacag aaacattttt  2100
atgttgttac ttatatacac ggttacagac tacacgagtt atatttgttg atattggaag   2160
cgttgaaact actgatagct gatactccct ccgttcgttt ttatttgttg ttattgacct   2220
ataatgtgct tactttgtct gttacttta attattggca gaaggtatat tcttagatgt    2280
tagatgtgta tagtgtttcc ctggaaattt gctgatgtac taactgctag ctgcaggcaa   2340
```

```
ttgagaggag gagaagtcgt ctgcagaatg ctgcagctca gcagcagatc cagtggacag    2400
aagacccttc ccgatctgtg gatccaataa ctccagtaca ggcagagcag ggtggtgtgc    2460
caacaactgt ggatggtcaa ggtgttggaa gccctgcaac ctgtttggag gatggcaagc    2520
tgaagacatc gtcctatcca tcatctgact gctccttgca ggccactcca tccaaaccaa    2580
acgatccagc tctcgcagat ctcgtggaga agaagctgtc cagctcgata gagcagatcg    2640
agaagatggt gcggcgaaac ctgaagagaa cttcgaaggc cgctcagcct tccaagagga    2700
ccatccagag gcgcgtcctg atgtccatgc gatgagctga gaaagctatc tgctctgcca    2760
tggcttccct tgtctgctgc tttcttagca gcaagtcgta accaaccatt acgccagttt    2820
tgcctgaagg aggggtgggg ccgtgggggc tcctggttct ctgcttgagg accccggggt    2880
atgcggctta ctactagctc tctgcttgag ggtacacatt atggtgactg cgtattttta    2940
atttgagaaa ttagtagttc tatgtatagt tttatagtgt ggaacggata tgagaaatta    3000
gtagcaattg tgacttcgac agcttgaata ctgttgttat ggagtagttc ctctatactg    3060
ttgtttccga gtaacataac acagttttgg ccatcagtaa tgga                     3104

<210> SEQ ID NO 2
<211> LENGTH: 1526
<212> TYPE: DNA
<213> ORGANISM: Zea mays

<400> SEQUENCE: 2
caacaaggac agagcagaaa cttagccaga gattcgtcca ggatagggc tgtatcgtag      60 ggagtagtcg ttgcggagat tgggtcgaag cggactggac aggagccgag caaactatct    120
gcagaagagg ttaaagggtt gccgtgcgga ctccggagct gtgagaatct accccgaggt    180
aagctcttag agtcgtagtc aaagaggaga agccaggccg ggaacaaaca gaaaagtgag    240
gagatttgtt ggtgcattag ctactcacgc gtcccctgaa attctgcttg ttaactccat    300
cctaaaattt attgtgtgga cccaggagaa gagcaacagg agtacaggac tcagtgcacc    360
aagaatagga aagagcaaag accataacag ttgtatgaga tactgtgatt tctgggttca    420
tttgtttatc tgattatgcg ttcttttggtc tcttgcatca ctcatgtggt tgtatgcact    480
cctccaggaa cttcaagatg cttgaagtga ggactgcaag aaggccggct ctcgccgaca    540
tctctggtgg tgggttcttt atgaggacag tagaatcgcc aggagctgtg ctggtgaatg    600
gtgctgtcaa gcggccggct cggcagtttc tatcaccttc aagcaacaag gagaatgtgc    660
caccagtggg agctttcagg gctacaccaa agaggaggac ccccttgcct gactggtacc    720
cgaggacacc actccgtgac atcacatcaa tcgtcaaggc aattgagagg aggagaagtc    780
gtctgcagaa tgctgcagct cagcagcaga tccagtggac agaagaccct tcccgatctg    840
tggatccaat aactccagta caggcagagc agggtggtgt gccaacaact gtggatggtc    900
aaggtgttgg aagccctgca acctgtttgg aggatggcaa gctgaagaca tcgtcctatc    960
catcatctga ctgctccttg caggccactc catccaaacc aaacgatcca gctctcgcag   1020
atctcgtgga gaagaagctg tccagctcga tagagcagat cgagaagatg gtgcggcgaa   1080
acctgaagag aacttcgaag gccgctcagc cttccaagag gaccatccag aggcgcgtcc   1140
tgatgtccat gcgatgagct gagaaagcta tgctctgc catggcttcc cttgtctgct   1200
gctttcttag cagcaagtcg taaccaacca ttacgccagt tttgcctgaa ggaggggtgg   1260
ggccgtgggg gctcctggtt ctctgcttga ggaccccggg gtatgcggct tactactagc   1320
tctctgcttg agggtacaca ttatggtgac tgcgtatttt taatttgaga aattagtagt   1380
```
tctatgtata gttttatagt gtggaacgga tatgagaaat tagtagcaat tgtgacttcg    1440
acagcttgaa tactgttgtt atggagtagt tcctctatac tgttgtttcc gagtaacata    1500
acacagtttt ggccatcagt aatgga                                        1526

<210> SEQ ID NO 3
<211> LENGTH: 684
<212> TYPE: DNA
<213> ORGANISM: Zea mays

<400> SEQUENCE: 3
atgcactcct ccaggaactt caagatgctt gaagtgagga ctgcaagaag gccggctctc      60
gccgacatct ctggtggtgg gttctttatg aggacagtag aatcgccagg agctgtgctg     120
gtgaatggtg ctgtcaagcg gccggctcgg cagtttctat cccttcaag caacaaggag      180 aatgtgccac cagtgggagc tttcagggct acaccaaaga ggaggacccc cttgcctgac     240
tggtacccga ggacaccact ccgtgacatc acatcaatcg tcaaggcaat tgagaggagg    300
agaagtcgtc tgcagaatgc tgcagctcag cagcagatcc agtggacaga agacccttcc    360
cgatctgtgg atccaataac tccagtacag gcagagcagg gtggtgtgcc aacaactgtg    420
gatggtcaag gtgttggaag ccctgcaacc tgtttggagg atggcaagct gaagacatcg    480
tcctatccat catctgactg ctccttgcag gccactccat ccaaaccaaa cgatccagct    540
ctcgcagatc tcgtggagaa gaagctgtcc agctcgatag agcagatcga gaagatggtg    600
cggcgaaacc tgaagagaac ttcgaaggcc gctcagcctt ccaagaggac catccagagg    660
cgcgtcctga tgtccatgcg atga                                          684

<210> SEQ ID NO 4
<211> LENGTH: 227
<212> TYPE: PRT
<213> ORGANISM: Zea mays

<400> SEQUENCE: 4

Met His Ser Ser Arg Asn Phe Lys Met Leu Glu Val Arg Thr Ala Arg
1               5                   10                  15

Arg Pro Ala Leu Ala Asp Ile Ser Gly Gly Gly Phe Phe Met Arg Thr
            20                  25                  30

Val Glu Ser Pro Gly Ala Val Leu Val Asn Gly Ala Val Lys Arg Pro
        35                  40                  45

Ala Arg Gln Phe Leu Ser Pro Ser Ser Asn Lys Glu Asn Val Pro Pro
    50                  55                  60

Val Gly Ala Phe Arg Ala Thr Pro Lys Arg Arg Thr Pro Leu Pro Asp
65                  70                  75                  80

Trp Tyr Pro Arg Thr Pro Leu Arg Asp Ile Thr Ser Ile Val Lys Ala
                85                  90                  95

Ile Glu Arg Arg Arg Ser Arg Leu Gln Asn Ala Ala Ala Gln Gln Gln
            100                 105                 110

Ile Gln Trp Thr Glu Asp Pro Ser Arg Ser Val Asp Pro Ile Thr Pro
        115                 120                 125

Val Gln Ala Glu Gln Gly Gly Val Pro Thr Thr Val Asp Gly Gln Gly
    130                 135                 140

Val Gly Ser Pro Ala Thr Cys Leu Glu Asp Gly Lys Leu Lys Thr Ser
145                 150                 155                 160

Ser Tyr Pro Ser Ser Asp Cys Ser Leu Gln Ala Thr Pro Ser Lys Pro
                165                 170                 175

Asn Asp Pro Ala Leu Ala Asp Leu Val Glu Lys Lys Leu Ser Ser Ser
            180                 185                 190

Ile Glu Gln Ile Glu Lys Met Val Arg Arg Asn Leu Lys Arg Thr Ser
        195                 200                 205

Lys Ala Ala Gln Pro Ser Lys Arg Thr Ile Gln Arg Arg Val Leu Met
    210                 215                 220

Ser Met Arg
225

<210> SEQ ID NO 5
<211> LENGTH: 2817
<212> TYPE: DNA
<213> ORGANISM: Zea mays

<400> SEQUENCE: 5

| | | | | | |
|---|---|---|---|---|---|
| gaccgtagca | gcgtagccag | tagcccagta | cccagtagta | cccagtagcc | atctccatcc | 60 |
| aggctcaaac | cctagggaat | ctacccagaa | atcacacccc | aagcagggtc | ctatcgtatc | 120 |
| aagaagccgt | cgcggggggcc | ggatcgccgc | ggctcggaga | ggagcggagc | gaaaatcgtg | 180 |
| agcaaccttt | gctgttctcc | agtggatatg | ttcttgcatc | ttttcgggcg | gttcgtgatt | 240 |
| cgattcttct | tgttggttc | tgttaccaca | gatctgcgga | caggtaagga | ttcggaggcg | 300 |
| ggatcaggag | ctgagggaac | ctgttcgagg | tgagaatcga | aggacagcag | ggggggtttg | 360 |
| gttggttctt | tcgtgggatt | tgttggttc | agcctccgtc | tctttgttct | tacgtgtttg | 420 |
| actggttatt | ttggttcgaa | tacctgccaa | ggatggggaa | tatgagtaga | gcggctggga | 480 |
| tttgcatggt | tttgatggtt | tccttgaagc | tcttgtctga | actgttgctc | ttgtttgcct | 540 |
| tgtgtttttc | ttgcaggtgg | cctagactcg | tagggatcgc | gttgacattg | ggagaaatca | 600 |
| cggagaggcg | gaaaccgagc | aatagccaat | aggtgcgtag | aatttggtga | ataggttgct | 660 |
| cacgtcctct | ctgaatattt | cttgacaatc | tggcaatttc | atccaaaaaa | aatatttcac | 720 |
| gcctccaggg | gaagggaaga | gcaacagtgc | ccggggcacc | aagaattcgt | tgcatagatc | 780 |
| caggagaaga | acaatagaaa | tctgggcaga | acgagagcag | aactgtaaga | aaatttatgg | 840 |
| tttcttggtc | catttactga | tgtgctgatt | cattgtctgg | ttggttcttg | aatcactgtc | 900 |
| tcaccgatat | gagctacaca | aacttctcgc | aggactacaa | gatgcctcaa | ttgagaactg | 960 |
| ccagcaggcc | ggcgctcgcc | agcaactctg | ctggtggttt | ttttatcagg | agaagggtgg | 1020 |
| catcaccagg | aacttcccag | gcaaagggcg | ccgccaagcc | gctggctcga | cgggtccgaa | 1080 |
| cacctgcagc | gagggctaaa | ccaaagagga | gaagcccct | acctgactgg | tacccaaggg | 1140 |
| tcccactccg | tgacatcaca | tcaatcgtaa | aggtggtgaa | ctatttccct | agactgtatt | 1200 |
| tggatgttcc | ataaatttct | ttaatattgt | gtatgttctg | tgctaatatt | atgccataaa | 1260 |
| cttcaccatg | ctagaactaa | tattgtgtaa | ccatgatttg | attgaggatg | acagtagcat | 1320 |
| gaaattgcag | gctaagcaaa | tctttttatgc | ttaatccagt | gattaacata | aaagttgttg | 1380 |
| tagttcaaat | ggattagcga | tgattttgtt | aggccaatca | gcaccctttt | gttttatttg | 1440 |
| attggatttt | gctgttctca | gtttatgcag | tcagcaatat | gaatgtgctt | aaaactagag | 1500 |
| aaaggtctga | tgctcccctc | tttcaaaatt | aagttgcttt | agttttgacc | taagccaaac | 1560 |
| tcttctaact | tgctcaagt | ttatagaaaa | aatatttaac | atatacaatt | tacggtacat | 1620 |
| aatgaatgcg | ttatttaaga | cttatttcat | tgtggattta | atgaaattaa | gttgatgttg | 1680 |
| tgatgttggt | gtgttttttct | ataggcataa | tcaattttaa | aacggtttga | cttagaacga | 1740 |

```
taaaagactt acatttttgg gaccgatgta gctagcagta tgcaataagg tcaatcttat    1800
cgatatattt tgcaccattt aatatatatt gctgctttgc aatcttgtaa atgcagtatc    1860
atcatgcact gaataacata tcatgttaga cgttcactaa catttcagta tttcactata    1920
ggtagtccat gcttttgttt gtcgatgcac actcaaaaat tgcttgtcca ccatgctact    1980
gtactaactg caatttacag gctcttgaga aagaaatcg cctagaggag gatgcggctc     2040
ggcaacacat ccaatcgaat gaagattctt cacagcctgt ggatccaaca actgcagaac    2100
atagtaatcc tgattctcaa agcacgcaaa ctcaagaaac accgggtgct gttgcttctg    2160
gtccaagctc aacttcagct gttgcaaacc gtgtgacttc tgtggctgag gcaagcaag    2220
aggcaacgga ctgctccttg caggtggctc catccaagcc aaatgatcca tctcccgctg    2280
atctggtgaa gaaactgtca ggttcgatag agcagattga aaagatggtg aggcgccata    2340
tgaaggaaac tcatccaaag gctgctcagc cttccaaggt agttgtccaa aggcgcatac    2400
tgatgtccat gcgatgagct cagcaacgat ttctcttgtc tgctgcgttc ttggccgcta    2460
gtcaaggtat gtctagggat ggggattcct ggttctctgc ttgaggacac tgtggtagga    2520
gtaaaagagg gatttctagc ttctctgctt gagagcatgg ctatctgttg gtacaacttg    2580
ccatggtatg cttactgcat acgacttcag ttggcttcac cagaaacgaa ccactgttgt    2640
tcacgtcttt ctgtttgtga agtataagac ttcactgcgt agtagtaagg cgtactagat    2700
atttgtggcg tttagttcac cgaaaagata gagcagttac gagttgtagt aacagcttga    2760
attcttgaca cttcaattga tacagttagc cttgcttatt gttccagatt ttggttg       2817
```

<210> SEQ ID NO 6
<211> LENGTH: 1464
<212> TYPE: DNA
<213> ORGANISM: Zea mays
<400> SEQUENCE: 6

```
gaccgtagca gcgtagccag tagcccagta cccagtagta cccagtagcc atctccatcc     60
aggctcaaac cctagggaat ctacccagaa atcacacccc aagcagggtc ctatcgtatc    120
aagaagccgt cgcgggggcc ggatcgccgc ggctcggaga ggagcggagc gaaaatcatc    180
tgcggacagg taaggattcg gaggcgggat caggagctga gggaacctgt tcgaggtggc    240
ctagactcgt agggatcgcg ttgacattgg gagaaatcac ggagaggcgg aaaccgagca    300
atagccaata ggggaaggga agagcaacag tgcccggggc accaagaatt cgttgcatag    360
atccaggaga agaacaatag aaatctgggc agaacgagag cagaactgac tacaagatgc    420
ctcaattgag aactgccagc aggccggcgc tcgccagcaa ctctgctggt ggttttttta    480
tcaggagaag ggtggcatca ccaggaactt cccaggcaaa gggcgccgcc aagccgctgg    540
ctcgacgggt ccgaacacct gcagcgaggg ctaaaccaaa gaggagaagc cccctacctg    600
actggtaccc aagggtccca ctccgtgaca tcacatcaat cgtaaaggct cttgagaaaa    660
gaaatcgcct agaggaggat gcggctcggc aacacatcca atcgaatgaa gattcttcac    720
agcctgtgga tccaacaact gcagaacata gtaatcctga ttctcaaagc acgcaaactc    780
aagaaacacc gggtgctgtt gcttctggtc caagctcaac ttcagctgtt gcaaaccgtg    840
tgacttctgt ggctgagggc aagcaagagg caacggactg ctccttgcag gtggctccat    900
ccaagccaaa tgatccatct cccgctgatc tggtgaagaa actgtcaggt tcgatagagc    960
agattgaaaa gatggtgagg cgccatatga aggaaactca tccaaaggct gctcagcctt   1020
ccaaggtagt tgtccaaagg cgcatactga tgtccatgcg atgagctcag caacgatttc   1080
```

```
tcttgtctgc tgcgttcttg gccgctagtc aaggtatgtc tagggatggg gattcctggt    1140
tctctgcttg aggacactgt ggtaggagta aagagggat ttctagcttc tctgcttgag    1200
agcatggcta tctgttggta caacttgcca tggtatgctt actgcatacg acttcagttg    1260
gcttcaccag aaacgaacca ctgttgttca cgtctttctg tttgtgaagt ataagacttc    1320
actgcgtagt agtaaggcgt actagatatt tgtggcgttt agttcaccga aaagatagag    1380
cagttacgag ttgtagtaac agcttgaatt cttgacactt caattgatac agttagcctt    1440
gcttattgtt ccagattttg gttg                                          1464
```

<210> SEQ ID NO 7
<211> LENGTH: 648
<212> TYPE: DNA
<213> ORGANISM: Zea mays

<400> SEQUENCE: 7

```
atgcctcaat tgagaactgc cagcaggccg gcgctcgcca gcaactctgc tggtggtttt      60
tttatcagga gaagggtggc atcaccagga acttcccagg caagggcgc cgccaagccg     120 ctggctcgac gggtccgaac acctgcagcg agggctaaac aaagaggag aagccccta     180 cctgactggt acccaagggt cccactccgt gacatcacat caatcgtaaa ggctcttgag    240
aaaagaaatc gcctagagga ggatgcggct cggcaacaca tccaatcgaa tgaagattct    300
tcacagcctg tggatccaac aactgcagaa catagtaatc ctgattctca aagcacgcaa    360
actcaagaaa caccgggtgc tgttgcttct ggtccaagct caacttcagc tgttgcaaac    420
cgtgtgactt ctgtggctga gggcaagcaa gaggcaacgg actgctcctt gcaggtggct    480
ccatccaagc caaatgatcc atctcccgct gatctggtga agaaactgtc aggttcgata    540
gagcagattg aaaagatggt gaggcgccat atgaaggaaa ctcatccaaa ggctgctcag    600
ccttccaagg tagttgtcca aaggcgcata ctgatgtcca tgcgatga                 648
```

<210> SEQ ID NO 8
<211> LENGTH: 215
<212> TYPE: PRT
<213> ORGANISM: Zea mays

<400> SEQUENCE: 8

```
Met Pro Gln Leu Arg Thr Ala Ser Arg Pro Ala Leu Ala Ser Asn Ser
1               5                   10                  15

Ala Gly Gly Phe Phe Ile Arg Arg Arg Val Ala Ser Pro Gly Thr Ser
            20                  25                  30

Gln Ala Lys Gly Ala Ala Lys Pro Leu Ala Arg Arg Val Arg Thr Pro
        35                  40                  45

Ala Ala Arg Ala Lys Pro Lys Arg Ser Pro Leu Pro Asp Trp Tyr
    50                  55                  60

Pro Arg Val Pro Leu Arg Asp Ile Thr Ser Ile Val Lys Ala Leu Glu
65                  70                  75                  80

Lys Arg Asn Arg Leu Glu Glu Asp Ala Ala Arg Gln His Ile Gln Ser
                85                  90                  95

Asn Glu Asp Ser Ser Gln Pro Val Asp Pro Thr Thr Ala Glu His Ser
            100                 105                 110

Asn Pro Asp Ser Gln Ser Thr Gln Thr Gln Glu Thr Pro Gly Ala Val
        115                 120                 125

Ala Ser Gly Pro Ser Ser Thr Ser Ala Val Ala Asn Arg Val Thr Ser
    130                 135                 140
```

```
Val Ala Glu Gly Lys Gln Glu Ala Thr Asp Cys Ser Leu Gln Val Ala
145                 150                 155                 160

Pro Ser Lys Pro Asn Asp Pro Ser Pro Ala Asp Leu Val Lys Lys Leu
            165                 170                 175

Ser Gly Ser Ile Glu Gln Ile Glu Lys Met Val Arg Arg His Met Lys
        180                 185                 190

Glu Thr His Pro Lys Ala Ala Gln Pro Ser Lys Val Val Val Gln Arg
        195                 200                 205

Arg Ile Leu Met Ser Met Arg
210                 215

<210> SEQ ID NO 9
<211> LENGTH: 16989
<212> TYPE: DNA
<213> ORGANISM: Zea mays
<220> FEATURE:
<221> NAME/KEY: misc_feature
<222> LOCATION: (10801)..(10900)
<223> OTHER INFORMATION: n is a, c, g, or t

<400> SEQUENCE: 9
cgagattacg agacaagaga caagtagaca acccagctct ccagcggtcc agcggtccag      60
cctctcctag ccgaggccaa aaccccata ccaacacaca cttcgcttct cgctgcctcc     120
gcggcggcgc gccgctccgc tccgagccct cttcctcctc ctcctctgcc cgttcggtcg     180
agaatgttct actcgcatca gcttctcgcg cggaaggcgc cgctcggcca gatatggcgc     240
gtctgctccc ttgatcgcac ctcctatgcc tctcgttgcg ggctctaatc gcgctcgttt     300
cccttccttg ttccttgcaa tgcgtttggt tctatgcctt atcctggcat cgacccacag     360
tgatggccac gctcgcgccg atttggcggt cactaactgc gtttgcattg tggtttcagg     420
atggcggcga cgctccactc gaagatcaac cgcaaacggc tcgacaagct cgacatcatc     480
aaaatctggt ggggaaactg gtcccaggga ttcgagttcc gcacggtttt gactgctatt     540
tttgtgtttt ttttatttgt ttttgctgac ttttgtttgt gtgtttcact tttagtgagg     600
aaattttgaa cccctcggtg cccatggctc tgaggctctc tggaatcctc atgggtgagt     660
tcgattttgc ttgcgccacc caaaactgtt cctcccattt tttggatagt tttttttac     720 gttccaattt ccatggtcga aaattcgaaa tgcgtgagca ggtggcgtgg tgatcgtgta     780
cgagaggaag gtgaagcttc tctacagtaa gtttcttcct ccctacatcc tacttgatgt     840
tgattttgtt tgaattccca gtgtttcatc atcccaattc taaatcgat catgtgttct     900 ctttctcgca gctgatgtct ctcggcttct ggtaagaact agttcaggat ctgcccgagt     960
gttttctgtg tcctggtcag tcgatttgaa tatccttgcg aattcagttc gagttatacc    1020
actaacttct cgtgcagact gagatcaacg aggcatggcg gatcaaaccg gtcacagacc    1080
ccaccgtcct ccccaagggt aaaactcaag ccaagtaagt gtgctaccgg tctcctccct    1140
ttctaagcgt ttatagatgt tacatgctgg ggttgagggg gttcggtttg agtaaggttg    1200
cactgcattc atgctgttga tgttgttatt gatgagactt ggtgtttgct tcttagcttt    1260
cttaaaacag agattgttgt gtgtgcgttt aggctgtgat gtgttcatct ggttgtttgg    1320
attggcgaat gttgtgatct ggctgagatg ttcatggaag ttcttaggag atagatatgt    1380
gttagtttgc ttgaactgaa ttggtatctg gtgcaatttg tgtgccgtgg gaaacgaaaa    1440
tgggattcac agctacatgt tggcgattcc cgtggtagtt tgttgtgcct tactcactgg    1500
gcccttgtgc ttgctgaagc actcacatcc actgtctgat actctgatat ctgatgtatg    1560
```

```
agtcccaatg atcttctgtc aactggccta atcacttgct gttttatttt tttatttata   1620
tttataattt tgactttga gatatcagaa taggaggtgg atggatttgc atttagcata    1680
ttttggtgca acagttactt tctccttcca atatgtgagc atcttcgtgt cgttggagta   1740
tcttttggca tattctttag cgtgtccatt tgctagctat acaatactgt acttgagaaa   1800
taatgctatc ttaaaagggt tttcattacc tttgagaact ggaaatgaac atccacggcc   1860
ttgattaatt cttttggcat taccattcct atggctgtag tataacccctt ggaaatttac  1920 ttgagaaatg taatcttttc ttgatatagc acatttcggg ttaaacttct atagataaat   1980
ttgacctcat tactactagc tctttcatag ccaaacacct aagtctctcc ccttgtgtaa   2040
atagcatgga gtggatatga accggtgata tgttatgtgg ggcgccactt acaggcgcag   2100
gcctaaggat aagagaccta gttgagttta tctagagata ttagtcaaga atatctaggg   2160
gtaatagcag attagaagtt gttgagatt tttaggagaa gtttaaggag atagagtcaa    2220
gcagatagga ggttgcggcc atgcaactgg cctatatatg taatggaaag ttatgaaata   2280
aaggaggaat gaattatctc caaactgtct ttcttccctc ctaatccggt ctccctcctt   2340
gctgcccaac atagatcagc acccaaccga tcgtccacgc cacatgcgaa gtcaggggcc   2400
ggcgcctgcg cccttgccac ttcccccata ccgtcggcca cataacatct tggtttcagg   2460
agaccagcca cgcacctacc caccaccatg tcctccatcc caagcgatcc agtggctcag   2520
gccttggacg ccatcaacca aaggctggca accctggaca ccctgcacac cactatacag   2580
cgcctagaac ggcagcaaca ggaaagctag gctgccattg atcgccttga ttagcgccag   2640
caggagatca tccctcacgg gaaccaacgt ccacgaggcg ggcccaatgc caaccatgaa   2700
gaccgcccaa ccagattcca tcatctggat ttcccacaat atgacgagaa gacggatccg   2760
ctactcttca ccaacaaatg cgagtcattc ttcttccagc agcgagtcgt tctagaggac   2820
aggtatggat ggtatcatac cacctggaaa acgctgcaca acagtggtac atgcaattgc   2880
accaggaaga agggacgccc cccttggcaa cgttttgccg agctgctgaa ccttagcttc   2940
gggcccccgt ccgagcctgc cccctcggcg aactagcgag ttgccggcgc acaggaacgg   3000
tggacgccta caccgagcac ttcctagagc tgctacccag ggctgggccg ttgagcatga   3060
atcaaaagat ccagctgttc accctgggat tacaggaacc actctccatc gacgtcgaac   3120
tccaacaccc ggtcacactg gaggtggcca tgagcctcgc cagagcctac aaacgccggg   3180
aacaggcagt tgcagcagca caggcgtcga ccaacaggcc accccgatct agtcgtggct   3240
tgcttccaac gctgtcgaca ccccagctgc caccactcgc tggctcagac tcgtcatcac   3300
cattatgcgc ccggccttcc agcagcagcg gacaggccat ccgtcggctc tcaccggagg   3360
agatggacga acgccgacgt ttgggacttt gcttcaacta tgatgagaaa tttgccagag   3420
gccacaaccg cgtctgcaaa catctcttcc tcaaactcca cgaaggcgag agcgacgacg   3480
gcaacacaga agaaccggcc agcaacaacc ccgtcatctc cctccatgcc atcgccgggg   3540
tcacggccaa caagaccatg caggttccgg tcagtctggg cacagtcagc atcgtcgccc   3600
tcatcgactc tagatctaca caactccatc tccaaagcca ccgccacacg aacaggtctc   3660
ccggtcgcgt aacgggggaa catgtgcatc atcgtggcta acggcgagaa gctgccatgc   3720 ctggagtct tcagatcagg gcccttcgtc atccacaaca ccaccttctc ggctgatctc    3780
atcgtcctgc ccctgccgg gttcgacatg gtactcggta cctagtggct cgccacgctg   3840
gggccgatcc tctgggactt cgccaagttg tccatggcgt tctggcgtga aggacgacag   3900
```

```
atggagtggc gaggactcgc agagacacca cgaccgcgcc tgctcgcagc aacaggccag      3960
gacgtcctcg acgctatgct cacctccttc gacgacctgt tccgcgagcc tcgtggccta      4020
ccgccgcagc gaccctgcga ccaccggatc catctactac cgaccacggc gcccatcgcc      4080
gtccagccgt accgataccc agcactgcaa aaggatgaat tggagcgcca gtgccacgac      4140
atgcagcagc atggattgat ctgccatagc acctcgactt tctgtctccg gttctcttgg      4200
tcaagaaatc ggacgagacc tggcgttttct cgtcgacta cagagccctc aacgaacgca      4260
acatcaagga ctccttcccc attccagtcg tcgacgagct gcttgatgaa cttcgcggcg      4320
ccaagttctt caccaagctc gacctccgct ccggctatca ccaagtgcgc atggccaccg      4380
acgacagcca aagacggcg ttccgaacac acgaaggcct gtacgagttc ctcgtaatgc      4440
cgtttggcct ctccaacgcg tcggcgacat tccagacgct catgaacacg gtccttcatc      4500
cgttccttcg gcgcttcgtc ttggtcgaca tcctcatcta cagcagcacc tggtccgaac      4560
atctgcatca cctgaggacc gtcttcaccg cgctcagcga ccactccctg gtgctcaaaa      4620
gatacaagtg ctccttcggc gcagcgtcga cctcctacct tggccacctc atctcggcgg      4680
aaggcgtggc catggacgtt gccaaagttc aagcagtggt tgattggctg ccaccacgat      4740
cggtccgagc actacgcgag ttcctgggac ttgtgggcta ctaccgcaag ttcataaagt      4800
catatggtga aatagcagca cccctcactg cgctactcaa gaagaatggc ttctcctgga      4860
ccgatcagac cacaacaaca ttcctccacc tgaagaaggc actcaacaca gctcctgtgc      4920
tcacccttcc agacttagga caagatttca ccatagagtg cgacgcctct ggagccggat      4980
ttggcgtcgt gctgcaccag ggagcagggc tggttgcctt cttcagccga gcactggcac      5040
ctcggcaccg cgacctcact gcctatgagc gggagctcat tgggttggta catgcggtac      5100
gacactgacg cccataccct tggggtcagc cattctccat tcggacagac cactacagtt      5160
tgaagtacct gctagatcag cgattgtcac atcccccaac accactgggt aagcaaactg      5220
cttgggtttg atttcagggt ggaataccga tcagggcgca acaacattgt tgcagacgcc      5280
ctgtcgcgcc gcgacatgga agacgctgca atcttctccc tgtcaggacc aacattccag      5340
gtgtttgatc aactccgcca ggcagcagca tctcagtcgg cccttgtcgc attgcgcgac      5400
gagatcctgg tcgacacacg caaaacacct tgggcgtttg tcgatggact cgtgttgttc      5460
aatggtcatg catatctccc tcccgagtct agcatcctcc aagacatact cgtgtcgact      5520
cacgacgtgg ggcatgaagg cacagagaag acactgcacc ggtttcgacg ggattttcac      5580
actccaaggg caagggctat cattaaggac ctggttcggc actgcatcac ctgctagtga      5640
aacaagactg aacatcttca tccagcaggc ctccttgccc ctctaccaat accaacgtca      5700
gtctggtcag atatatcaat ggacttcatc gaaggccttc ccaaggttgg gggcaagtct      5760
gtcatcctgt caatttattc agcagaaaca atagcatcaa tcttcttctc ggaggtagtc      5820
agactccatg gcctcccatc aaccatagtg tcagatcgtg atccagtgtt cacatccaca      5880
ttttggacaa cactcttcaa gttgatgggc accaagctac acatgagttc cgcattccac      5940
ccccagtcgg atggtcaaac agaaacaatc aacaagacca ttggcatgta cctctggtgt      6000
ttgacaggtg accgtccccg acaatggctg cgatggctcc cttgggcaga atatgtctat      6060
aacacctcct tccgcactgc cctcaaggag actccccttcc gcatcatata tggtagggat      6120
ccaccagcat tacgagagta tgacctggga gagtgccgag taccagcagt tacccagtcc      6180
atgacagaaa gagaagaatt cttgagtgat gtacgcgccc gactgagca ggcacaggcc      6240
gtagccaaac gtgcctacga ccgtggtcac agggcagtga gcttctctcc aggtgattgg      6300
```

```
gtatggttgc gagttcgtca tcgctctcca gcaacgctct cagcggtgat gcgcggcaag    6360
ctgaggccgc gctactttgg gccatacaag gtggcggcca tgatcaatga ggtggcttat    6420
cgcctcgaac tgccatccac ggctcggatt cacaacgtgt tccacattgg gttactaaag    6480
aaatttctgg gcactccaga ttctccacca ccactcccgc cgattcatga cggtgctgca    6540
cagctgcaac cagcacaggc tgaagattcg tcaagccaga ggactttgct agatccttat    6600
tcagtgggat tcattgccta gctcagcagc aacttgggaa gacctggacg acttcaggag    6660
gcaatatcct cattttcagc tcgaggacga gctgatactc gatgggggaa gagatgttat    6720
gtggggcgcc acttacaggc gcagggctaa ggataagagg cctagttgag tttatctaga    6780
gatattagtt gagaatatct aggggtaata gcagattaga agctgttgag atttttaggg    6840
agaagtttaa ggagatagag tcaagcagat aggaggctgc ggccaggcag ctggcctata    6900
tatgtaattg aaagttatga aataaaggag gaatgagtta tctccaaact gtctttcttc    6960
cctgctaatc cggtctccct ccttgctgcc caacatagat cggcacccag ccgatcgtcc    7020
acgccacctg cgaagtcagg ggccggcgcc tgcgcccttg ccacttcccc cctaccgccg    7080
gccacataac atgatatagg aaagattttc ttttcgaaga gtaagaaagt gatgtggcat    7140
gcttatctga cagccgaact tcatgcaggt atgaagcagt aacactgcca gagatcaata    7200
tggtggtgga acagcccatg ttttctcag agcctgatgg tgccaagttc cgacgaatgg    7260
taatccttgt cacctgtgta tttcagaaaa aaaaacttta tatgcataca gtatggtgct    7320
tatttagaat aaccatcgca tgaacacctc acttttttct gactttggcc tgattgtatc    7380
cactcttctg actgaaatgt atcatgcatg cttagggatt ggaagatctg gatgaacagt    7440
atgttcaagt caatcttgat gatgatgact tctctcatgc tgatgatcgt catcaaggtt    7500
ggtctttctc atcttgcgga ttactctgtg tttgtatagg ggtgaatatt ttcaaactct    7560
acaatatttt ctcagctaaa gcagtgaata taaccctggt cgataatttt gagtctgggc    7620
ttgcagaaac tgatttattc aatcactttg agaggtaaag aaaagctgca tatttatta    7680 aatttaccac tcttttatca tcgctgctgc atgtttcttt ttcttatttt gcttatagta    7740
caaatataaa tagtgccttg tatacagatt tgacatagca gatgatgaga ccacagtcaa    7800
tatcactcct gatgagtacc cacaagttcc aagtacgctg attccgtcac cacctaggca    7860
ggaagacatt cctcaacaag aagaaccgta ctacgctgcc ccctcccctg ttcatggaga    7920
acctcaacaa ggtgaaacca aacacatgat ttactctctg ccatatggaa acaaggccgt    7980
aacttaaaaa aatatagaat ttccttttcc ccccaaagga caatgatttt tatgtcaatt    8040
gtgcattgac atgtaatttc gcaagaggaa cttgcatcca aaagttctcc agatgatggt    8100
tcttactggc agctaatggt catttgcaga ctctattgga gtattccaaa aacaattcac    8160
actttatctc tcattgcctt tgtacatact caaatggcta cagtaggact ttttttaggat   8220 taaaggctag ggagagcatc tttcttttga cgagttgggg aggcgggggg tatagtttct    8280
gtcggagggg agaatccttc ggccgagtgg tggattgcac ctgccctgat cctcagatga    8340
ggagtaggct taggtgattg cctggccttc tagatgaaca caagggttta gagtggttca    8400
ggtcgtcgga gcgtattacc ctacatccac tgtgagttgt attgcttgag aactggggag    8460
tcgaaggtct gagtgtgaat tggcctcccc tgctacggaa caagtactct ccctttttata   8520 gtctaaggca gacacattac aagggagttc aggccttgac aggtggacct aggagagttt    8580
acaatatgga gcggtaaaca actggatagc gctgacaacg ctagatcttc ttgagctcgt    8640
```

```
atcccttctt gggtactact ccagcttctg gcgtccttat cttgccacct tgtcatgtct    8700
aatcggaaca taggccttga tgtaggttgc gacgtagtct gatacgttgt tgtgcgtagg    8760
gtgtgatgaa tggtgtcgtc cagtcttctc cgtccgtccc ttcatgcctc ggtaacacac    8820
gaggcacaat ggaagtcata atgaaggacg cctaaacgac gcattaggtc aatgcccttg    8880
cctcggtaac atgcgggtaa cagtaaaatc cacacgttac aggcctgaga tgtagcgtgc    8940
attaaatgcc agggacacgt gttggggcga aggctcaacg ccccctcgct cgggaaacca    9000
caataacgaa gggtcaagga ctggagggtg cgaaggcctg aagagcgacc acgcttcgaa    9060
gaacacgaag agtccgaaga ctcgggcacc cctttcacca ggacgggcca gagcgaagac    9120
catcgagaat tccgtcggcg gaggatatgg actgcgaaga ccatgcgctg tgatctaccg    9180
ccaattgtaa taggggggcc catgtgtagt cggcccacgc tgtgagatct agctcgcagg    9240
ccgctacgca agtaggactg ttagcggatc agcccgtgtt tgtaattaat tacgctgtaa    9300
tgacccactg taaccccca aggggaata ttccggggat atcgtaggta accgagggta    9360
catttgtatt tgacggggca gtgccgaccc tcggttacct ataaatacccc tcgtactgca    9420 ccattgtggg ggacggagaa aaacaatatt gccctaataa tttgtgttaa acgacatcaa    9480 attgttcct attcttccac tgttcgagct ggctgaccg cgagttagcg agttccaaca    9540
acacgctacc tgctattgat gcaggcaagt atacgtctca tctgtactca atgctggcgg    9600
gccctatgtc agaggctttc gccagacatc gcccgatggc ttacactagg ggcgtctggc    9660
cacgtgttaa caccggaccc ttgcctaggt gaggggcaga cctggggata agtggtgaca    9720
ctgcttccca tgtctttcct aaccatgggc tcgagtcgta cctgaggtga ttcgggctac    9780
tgttgccctt gcctggacac gtggtgactc cagtcctcac ctggcctgag gtacgaatgg    9840
tatctttcat acccggaatc gttctaaaga cttggtgttg taaccagaga gcgccttctc    9900
ctatgtctcc tccagatccc tttggttggg gatccgttgg gacacaagga gatctgtgtc    9960
ctatttgcag ggtcccaaac ctatagctga ggttgttgat tcctcccttt atggggcttg   10020
atgcagacga cgacccagcc ctggaggcaa gcctggcctg gtcatgactc catacggtgg   10080
gccttagccc cgtgctgggc cgactgcccg tgaaatcctt aacagtggcc cccaatgact   10140
caccttgaca tagcaggagt gggtaccccg ttttcagggt agcgacagtg gcccctgggc   10200
tcacctcggg tgaggcggca aacccgcagg tggggccata ccgtcttgtt ccagaaatgt   10260
caaccttgtg cagcagcttc gtgcatgtag ccttcacgtt gagtgggttg cttgccggca   10320
cactgttatt gctgcatgaa gacaaagaaa gtggtactgc cctcgtgttt atccagttat   10380
gggaaggcaa ggattatttt cttttccgcc ccagccgcta aggctccctg aagttttcc   10440 cagttgtggg ggattgcttt tagtccaggg agctactccg gagttcgact taggaatagt   10500
gcttaggagc atatggtatt ccgtgaatgg tttaggagta gtgcttagcg gtgtaccctc   10560
gagatcctag ctttgttgta ctcattctat tgaattatgt agccgggttg ttgctaggca   10620
gagtttataa gatccaacct taattttgaa tgaggcgtag gcccgttagg tacctagtcc   10680
aaaaagtact aagccagcta ttctgggacg gtggaaggtg taggcgtacg acacaggacc   10740
aggctaagcg gctacctagc tccggaccac ctgctagaat gtggacttt cctttagacc   10800 nnnnnnnnnn nnnnnnnnnn nnnnnnnnnn nnnnnnnnnn nnnnnnnnnn nnnnnnnnnn   10860
nnnnnnnnnn nnnnnnnnnn nnnnnnnnnn nnnnnnnnnn ctatcgtctt cttggagcac   10920
acaccggtct ctactccagc cgcaacattc gcaccatcat gacgttgcga ctgcgggggg   10980
atttcaaccc gtcggcttct accttcggcc tctactccag tctcatcgtg tgtggtgccc   11040
```

```
ccgttgcgac tgcgggggga tgttagacta tgtgtgtgtg agtgtgtgtg ggtcggcacc    11100
actgttgggc tgccggccca ttagggttag ggtttcctgt gtctctatat attgtaacct    11160
catctattat caatacaaca gttcatcttc cctcatttcc aactttgttt tttttgttgg    11220
ttgactagtt acctgatata ttacaaactg gctgctcgac ataatttaag tacatgtgtt    11280
gttgcattta tgccatattt gaagcatctt gctgcaatta ctgaaagttc tcttgcaggg    11340
ggaccagagg accaagagga acagaagatg aaggtaaaca tgatttatca agccttatta    11400
catctagaaa atagtatgaa aagggattac ttgtttactt gagctagcac ttttacacac    11460
agcagcaacc accgaaagca tcaaagcgga aagcacgttg ggaagtccca cgagtaatta    11520
tggacaataa ccagatgatg atcccaggaa acatatatca gacatggctg aaggatgcat    11580
caagccttgt ctcaaaaagg cgtaaactta acagcgtatg tttggctcga ctaacctatt    11640
ttcctggaga tttctgtacc gatgcattct aataaacaac atttatctga tttatgcttg    11700
cagaatttta attttattcg atcaaccaag ataagtgatc tcatgcacat ccccccggtt    11760
gctctaatat ctcatgacaa cttgttctca gaattatgtt atcctaagcc acttatgcag    11820
ctctggaagg actgcactga ggtcaagtcc acaaaagctt cttcaggtca cttcataatt    11880
tgtaatatca tgtcactctt gactaaagaa accatattat tttaacatgc taaaggccaa    11940
ttgaaaaacc ttaactgttt cttactttct taaaggaggg cagcgatcat catcacaaga    12000
accacaaccg aaaaactcac cacctcaggt tattctagat tcttttcaga aagaaaaac    12060 acccttccct agtgactcat cataattatc attaaatttg tccctggtga gtggttgaat    12120
tttcaggctg ggggagagta tgagatggaa acaggtggtc tgccgatgga tttaacagat    12180
ggcattgaaa aactcagggc aaacatgagt gcaaaatatg acagagctta caatattctt    12240
cacagtgacc atagtgttac tcctggaagt cctggtaagt tgaaaagtga ataagtttaa    12300
tttctgtctg tgcttatata gacagttgat gacgtaaatc tctagcaggg ttaagtcgca    12360
ggtctgcttc aagctctggt ggctctggat cggcgtttat acaattggat ccagaagtac    12420
aattgccatc aggaagtgga aggtgactgt tgacttatag taacagcagc atgtcaccta    12480
tatactgaac tatgactatg tgatattttg gtactgaaag aacttgtcca tctaaagttg    12540
ttttcgtcat cacaacagaa cctcttattg tatatgctcg taactagtga gtgcagaaac    12600
taaagtgtgt aatctccttg atgaagtggc aggcaaataa aaaaaatgtc tagctcccca    12660
ctgtccttca gtgtctttgt tagtttctta aagtgaccat gtcatggtta ttgaacacag    12720
gtccaaaagg gggcagcatt catctgcaag aagcttgggg aatcttgata ctgttgagga    12780
agattttcca ctggagcagg aagtgaggga cttcaagatg agaaggcttt cagattatgt    12840
gccaactcct ggttggttgc attctgtcct ttgctatata taaacatgtg aaactgtctc    12900
tggacgactg gaacataaac tgtttcaacc aacatagaag ttaacaattt tactccaact    12960
cctggttggt tccatttctg tcatttattt actctgttat atataaacat gtgaaactgt    13020
tttctggagc atttgaaact gtttcaacca acatagaatt taattgttgg cattcgtttc    13080
agacctactg gaagaaactg aaccgactca aaccccatat gagaggcgct ccaatccaat    13140
ggacaagatc acagaaacaa tccagtcgta atatcctta atttgtttgc tcatagtgcc    13200
tgggtcataa attatctgat gctagagtta tcttcatgca ggcatctcaa acttcatttc    13260 gatacccag gtgtcccaca atctgaatcc ttaagtcatt tagctcatgg aatgaccaaa    13320
gccagggcag cccgactatt ctatcaaata gctggtatgt attccctccg tcccaaatta    13380
```

```
taggtcattt tttgtttttc taggtacata acttttgttg acctataatt tgaaagctag   13440
gtagtatttc tctatggtgc tttgactgga aaatgaagag tactgttgtt aaagtaaata   13500
aaaaactagt agtggtcact gagatgatgt taaacagtta tgatagcttt actggcttag   13560
tgatggtttc tgtaattagg ttgggttaca attaaacacc attcaagcct gctttccttt   13620
tactgctagg aaatttggca caatttcctc aaatttgtta ttttagtgac cgtgtaacgt   13680
tttctcagtt actcagtatg gtgcaaataa ctattttttt attttttat aagatggttg    13740
ttgctctacc tttgcattgt agaagtttaa aaaacgcgaa aaaaactcta cctgagttag   13800
ttacttggtc tgagtagcac tccttaagtt ggttatatgg tctgagcgaa cactcctcag   13860
gttttaagtt cgactcacat ggggtatggt gtcgttgtgt acgggtgtga caggggtttg   13920
aaggtttttt cgacctgtgc aaggtcttct tattaatata atgtctggag gttgtgtttc   13980
cctccgcagg tcaagttttt atgtgaagtt taagaaaaaa acagtttgga aactcaaatc   14040
ccctaggaat ctctacattt ttcccaaggt gaacaatctc atggatacca ttggttttct   14100
tttcccgggt tcgtctcccc ttagctccaa actagcccct atcgaggagg gtgacgcatt   14160
agttttcagg tcttggttgt gtccaggttt gttgttgatg tttagctgga tgaagttgtt   14220
agttattaga gccattgtca aaacattgcc agcaacgcat aactggtttc tctcaattgt   14280
ggttaaaaag agaagtttca cacaacccaa tactaggccg cataagggtc cgttcgtttt   14340
ctctccaatc cggggattgt ggatgagttt caatccatag caagtcaaaa tctctactat   14400
ttttttttaa tcttattcaa tatatgtgat atagaaataa ccgaacaagg cctaactggg   14460
aacacggagt ttgcttaaaa tatttgacat aagaggaata acggtgaatc tgaagtttat   14520
ggtatttcat tgtaattgct agaatggagc ttattattta atgggaatgc ttgttctgca   14580
gttttggcaa cttgtgatta catcaaggtt actcagctgg aacggaaagg agatgaactg   14640
tacggagaca tcttgatctc cagaggatta aagatgtgac ttggtgatgt tggaaacaat   14700
tttgctgcgg tggttcccgg tgcacatctc gtgtttatat tacagaatgc ttacatattg   14760
cataggatgt cttgtagtta acacataatc tatacatggt gatctggtga agaaaggga    14820
gcgagatatg aggcagtagt tttgtgttat gtggcaagca aaattctaag ctgttatttt   14880
agaggtttca taatttaagt acgaacatgt gttatactat tatgaaacta agttgtcctg   14940
aaagcactta ctgaaaggga gaaatttaca tggtaccttg tcaacgatga aacatacatc   15000
ggaggacaac ataaagatgc acactgtatc ctgctcttcg gctgcttcat gttacgatac   15060
ctgtccattt gccctatctt tcatttttta tgggtggctt tgtcctattc taaatgcacc   15120
ttacttagca atctgatatt ttttcgcctg gaaataaatc acatgtatga ctgatgtatc   15180
tctgtctcta atctctaata tattaagcca ccagtttcaa cggttgtgac ttcttttttac   15240
aaagaatccc ttgtagttcg tcaaaataaa cctgcggtcc tagatcattt cacatcccta   15300
tcctatttgt tcgtagagta gcgttctcgc aactgtcact ctagcaacaa accccgtcca   15360
tttcgcaaca acctctgccc gcttcttccg tcgttgcacc gccatcggtg aggaggatta   15420
gggcgcccgc cttcggatat ggatgctcac taattgcctg tttggttggg ttctccccgt   15480
agcccggctg catgagacag gccggcggga gcttggctcc agagatgcga ccaatttgct   15540
cgcgcctgca gagcctagtc cagggtgctt taagtattgt gcgagtctgg ctccacatct   15600
gcacgcaggt aaccaaacac atacttcgca tgcgtagagc ctgattgaca acaaccaaac   15660
accagctcat tatatcccgc gatgcaagca ccagcaaata caggcaacca aacatatggt   15720
aagtgatata ggtggtgtcg agtccagcca actctgaacc tcctcgttgc ccctagggac   15780
```

```
cgggagtccg cctcctagct cactcgtctt ctactctggc gcgagctttt acaaagaacc  15840
ccttatattt cttcaaaatc aatccacggt cccagatcat attccatctc tatcctattt  15900
gttcgcacag tagcgttttc gcatatgtcg ctctagcaac aaacctcgtc catttcgcaa  15960
caaacttcgc ccgctttttc cgtcgttgca ccaccgctgg tgagaaggat tagggcgctc  16020

gcctccggat aaggatgctc actggatgat aaaagttgtg tcgaatccag ccaactctaa  16080
acctcttcgt cactcctagg gaccaggagc ctgtctccta gctcacccgt cttctgctcc  16140
gctcctccca ccccatggcg acgtggcatc aacggtagat ctacctagcg tgtgcttcat  16200
ctggtcacag ttgttctcgt cggatctatt attggtagag attgctctaa ttgtcgtgtt  16260
tttcgcaggg gacgtccact caccaggata caagcttctc aaataagcaa gccaagctgc  16320
tcaagacgta gaagttcgcg tccgagtttg accatctggt cagttcattc tttcactcat  16380
accctttgtt tgtcgatact tttagagata tatagctatt gaatgcagag gcttcctctg  16440
attcggcgat tttgtgcttg gtaggtggat acgtcaaagg tcaagttgga cgtgatgaag  16500
ctctggattg ccaagcgggt cattgagcta cttgggttcg acgtatgttt ctgatccatg  16560
cagaggtagt tgcatttttc actgaaaatt agcccaggtg ctacggtcat cttgttgttt  16620
gtgaccatgt tccctttttc ttcttttttg ttgggtcttt acttaacgag aaccctaact  16680
catttaccat tgtgatagga ccaaaattga agtccaaact ttgcactaca tctacagaac  16740
gtttgctttg gtgtcccgtt ccaatatgtt gcatgcttag agtttaagac acgatgctca  16800
agcaatgtac tggcacacag agttgcaatt gcaggcagct gcgcttgcac tacacatgtg  16860
caaacaattc caacagaata atatatagta gtacccccta tgcagcaccc gctgtaatac  16920
atggatcaca ctatttcatc agttataaat accatgagat gaatccagaa gaaaaaaaag  16980
ttgtatgtt                                                          16989
```

```

<210> SEQ ID NO 10
<211> LENGTH: 2514
<212> TYPE: DNA
<213> ORGANISM: Zea mays

<400> SEQUENCE: 10
cgagattacg agacaagaga caagtagaca acccagctct ccagcggtcc agcggtccag     60
cctctcctag ccgaggccaa aacccccata ccaacacaca cttcgcttct cgctgcctcc    120
gcggcggcgc gccgctccgc tccgagccct cttcctcctc ctcctctgcc cgttcggtcg    180
agaatgttct actcgcatca gcttctcgcg cggaaggcgc cgctcggcca gatatggatg    240
gcggcgacgc tccactcgaa gatcaaccgc aaacggctcg acaagctcga catcatcaaa    300
atctgtgagg aaattttgaa cccctcggtg cccatggctc tgaggctctc tggaatcctc    360
atgggtggcg tggtgatcgt gtacgagagg aaggtgaagc ttctctacac tgatgtctct    420
cggcttctga ctgagatcaa cgaggcatgg cggatcaaac cggtcacaga ccccaccgtc    480
ctccccaagg gtaaaactca agccaagtat gaagcagtaa cactgccaga gatcaatatg    540
gtggtggaac agcccatgtt tttctcagag cctgatggtg ccaagttccg acgaatggga    600
ttggaagatc tggatgaaca gtatgttcaa gtcaatcttg atgatgatga cttctctcat    660
gctgatgatc gtcatcaagc taaagcagtg aatataaccc tggtcgataa ttttgagtct    720
gggcttgcag aaactgattt attcaatcac tttgagagat ttgacatagc agatgatgag    780
accacagtca atatcactcc tgatgagtac ccacaagttc caagtacgct gattccgtca    840
```

| | |
|---|---|
| ccacctaggc aggaagacat tcctcaacaa gaagaaccgt actacgctgc cccctcccct | 900 |
| gttcatggag aacctcaaca aggggggacca gaggaccaag aggaacagaa gatgaagcaa | 960 |
| ccaccgaaag catcaaagcg gaaagcacgt tgggaagtcc cacgagtaat tatggacaat | 1020 |
| aaccagatga tgatcccagg aaacatatat cagacatggc tgaaggatgc atcaagcctt | 1080 |
| gtctcaaaaa ggcgtaaact aacagcaat tttaatttta ttcgatcaac caagataagt | 1140 |
| gatctcatgc acatccccc ggttgctcta atatctcatg acaacttgtt ctcagaatta | 1200 |
| tgttatccta agccacttat gcagctctgg aaggactgca ctgaggtcaa gtccacaaaa | 1260 |
| gcttcttcag gagggcagcg atcatcatca caagaaccac aaccgaaaaa ctcaccacct | 1320 |
| caggctgggg gagagtatga gatggaaaca ggtggtctgc cgatggattt aacagatggc | 1380 |
| attgaaaaac tcagggcaaa catgagtgca aaatatgaca gagcttacaa tattcttcac | 1440 |
| agtgaccata gtgttactcc tggaagtcct gggttaagtc gcaggtctgc ttcaagctct | 1500 |
| ggtggctctg gatcggcgtt tatacaattg gatccagaag tacaattgcc atcaggaagt | 1560 |
| ggaaggtcca aaaggggggca gcattcatct gcaagaagct tggggaatct tgatactgtt | 1620 |
| gaggaagatt ttccactgga gcaggaagtg agggacttca agatgagaag gctttcagat | 1680 |
| tatgtgccaa ctcctgacct actgaaggaa actgaaccga ctcaaacccc atatgagagg | 1740 |
| cgctccaatc caatggacaa gatcacagaa acaatccagt cgcatctcaa acttcatttc | 1800 |
| gatacccag gtgtcccaca atctgaatcc ttaagtcatt tagctcatgg aatgaccaaa | 1860 |
| gccagggcag cccgactatt ctatcaaata gctgttttgg caacttgtga ttacatcaag | 1920 |
| gttactcagc tggaacggaa aggagatgaa ctgtacggag acatcttgat ctccagagga | 1980 |
| ttaaagatgt gacttggtga tgttggaaac aattttgctg cggtggttcc cggggacgtc | 2040 |
| cactcaccag gatacaagct tctcaaataa gcaagccaag ctgctcaaga cgtagaagtt | 2100 |
| cgcgtccgag tttgaccatc tggtggatac gtcaaaggtc aagttggacg tgatgaagct | 2160 |
| ctggattgcc aagcgggtca ttgagctact tgggttcgac gtatgtttct gatccatgca | 2220 |
| gaggaccaaa attgaagtcc aaactttgca ctacatctac agaacgtttg ctttggtgtc | 2280 |
| ccgttccaat atgttgcatg cttagagttt aagcacacgat gctcaagcaa tgtactggca | 2340 |
| cacagagttg caattgcagg cagctgcgct tgcactacac atgtgcaaac aattccaaca | 2400 |
| gaataatata tagtagtacc ccctatgcag caccgctgt aatacatgga tcacactatt | 2460 |
| tcatcagtta taaataccat gagatgaatc cagaagaaaa aaaagttgta tgtt | 2514 |

<210> SEQ ID NO 11
<211> LENGTH: 1809
<212> TYPE: DNA
<213> ORGANISM: Zea mays

<400> SEQUENCE: 11

| | |
|---|---|
| atgttctact cgcatcagct tctcgcgcgg aaggcgccgc tcggccagat atggatggcg | 60 |
| gcgacgctcc actcgaagat caaccgcaaa cggctcgaca agctcgacat catcaaaatc | 120 |
| tgtgaggaaa ttttgaaccc ctcggtgccc atggctctga ggctctctgg aatcctcatg | 180 |
| ggtggcgtgg tgatcgtgta cgagaggaag gtgaagcttc tctacactga tgtctctcgg | 240 |
| cttctgactg agatcaacga ggcatggcgg atcaaaccgg tcacagaccc caccgtcctc | 300 |
| cccaagggta aaactcaagc caagtatgaa gcagtaacac tgccagagat caatatggtg | 360 |
| gtggaacagc ccatgttttt ctcagagcct gatggtgcca gttccgacg aatgggattg | 420 |
| gaagatctgg atgaacagta tgttcaagtc aatcttgatg atgatgactt ctctcatgct | 480 |

```
gatgatcgtc atcaagctaa agcagtgaat ataaccctgg tcgataattt tgagtctggg    540
cttgcagaaa ctgatttatt caatcacttt gagagatttg acatagcaga tgatgagacc    600
acagtcaata tcactcctga tgagtaccca caagttccaa gtacgctgat tccgtcacca    660
cctaggcagg aagacattcc tcaacaagaa gaaccgtact acgctgcccc ctcccctgtt    720
catggagaac ctcaacaagg gggaccagag gaccaagagg aacagaagat gaagcaacca    780
ccgaaagcat caaagcggaa agcacgttgg gaagtcccac gagtaattat ggacaataac    840
cagatgatga tcccaggaaa catatatcag acatggctga aggatgcatc aagccttgtc    900
tcaaaaaggc gtaaacttaa cagcaatttt aattttattc gatcaaccaa gataagtgat    960
ctcatgcaca tcccccggt tgctctaata tctcatgaca acttgttctc agaattatgt   1020
tatcctaagc cacttatgca gctctggaag gactgcactg aggtcaagtc cacaaaagct   1080
tcttcaggag ggcagcgatc atcatcacaa gaaccacaac cgaaaaactc accacctcag   1140
gctgggggag agtatgagat ggaaacaggt ggtctgccga tggatttaac agatggcatt   1200
gaaaaactca gggcaaacat gagtgcaaaa tatgacagag cttacaatat tcttcacagt   1260
gaccatagtg ttactcctgg aagtcctggg ttaagtcgca ggtctgcttc aagctctggt   1320
ggctctggat cggcgtttat acaattggat ccagaagtac aattgccatc aggaagtgga   1380
aggtccaaaa gggggcagca ttcatctgca agaagcttgg ggaatcttga tactgttgag   1440
gaagattttc cactggagca ggaagtgagg gacttcaaga tgagaaggct ttcagattat   1500
gtgccaactc ctgacctact ggaagaaact gaaccgactc aaaccccata tgagaggcgc   1560
tccaatccaa tggacaagat cacagaaaca atccagtcgc atctcaaact tcatttcgat   1620
accccaggtg tcccacaatc tgaatcctta agtcatttag ctcatggaat gaccaaagcc   1680
agggcagccc gactattcta tcaaatagct gttttggcaa cttgtgatta catcaaggtt   1740
actcagctgg aacggaaagg agatgaactg tacggagaca tcttgatctc cagaggatta   1800
aagatgtga                                                           1809
```

<210> SEQ ID NO 12
<211> LENGTH: 602
<212> TYPE: PRT
<213> ORGANISM: Zea mays

<400> SEQUENCE: 12

```
Met Phe Tyr Ser His Gln Leu Leu Ala Arg Lys Ala Pro Leu Gly Gln
 1               5                  10                  15

Ile Trp Met Ala Ala Thr Leu His Ser Lys Ile Asn Arg Lys Arg Leu
            20                  25                  30

Asp Lys Leu Asp Ile Ile Lys Ile Cys Glu Glu Ile Leu Asn Pro Ser
        35                  40                  45

Val Pro Met Ala Leu Arg Leu Ser Gly Ile Leu Met Gly Gly Val Val
    50                  55                  60

Ile Val Tyr Glu Arg Lys Val Lys Leu Leu Tyr Thr Asp Val Ser Arg
65                  70                  75                  80

Leu Leu Thr Glu Ile Asn Glu Ala Trp Arg Ile Lys Pro Val Thr Asp
                85                  90                  95

Pro Thr Val Leu Pro Lys Gly Lys Thr Gln Ala Lys Tyr Glu Ala Val
            100                 105                 110

Thr Leu Pro Glu Ile Asn Met Val Val Glu Gln Pro Met Phe Phe Ser
        115                 120                 125
```

```
Glu Pro Asp Gly Ala Lys Phe Arg Arg Met Gly Leu Glu Asp Leu Asp
         130                 135                 140
Glu Gln Tyr Val Gln Val Asn Leu Asp Asp Asp Phe Ser His Ala
145                 150                 155                 160
Asp Asp Arg His Gln Ala Lys Ala Val Asn Ile Thr Leu Val Asp Asn
                 165                 170                 175
Phe Glu Ser Gly Leu Ala Glu Thr Asp Leu Phe Asn His Phe Glu Arg
             180                 185                 190
Phe Asp Ile Ala Asp Asp Glu Thr Val Asn Ile Thr Pro Asp Glu
         195                 200                 205
Tyr Pro Gln Val Pro Ser Thr Leu Ile Pro Ser Pro Arg Gln Glu
210                 215                 220
Asp Ile Pro Gln Gln Glu Pro Tyr Tyr Ala Ala Pro Ser Pro Val
225                 230                 235                 240
His Gly Glu Pro Gln Gln Gly Gly Pro Glu Asp Gln Glu Gln Lys
                 245                 250                 255
Met Lys Gln Pro Pro Lys Ala Ser Lys Arg Lys Ala Arg Trp Glu Val
             260                 265                 270
Pro Arg Val Ile Met Asp Asn Asn Gln Met Met Ile Pro Gly Asn Ile
         275                 280                 285
Tyr Gln Thr Trp Leu Lys Asp Ala Ser Ser Leu Val Ser Lys Arg Arg
         290                 295                 300
Lys Leu Asn Ser Asn Phe Asn Phe Ile Arg Ser Thr Lys Ile Ser Asp
305                 310                 315                 320
Leu Met His Ile Pro Pro Val Ala Leu Ile Ser His Asp Asn Leu Phe
                 325                 330                 335
Ser Glu Leu Cys Tyr Pro Lys Pro Leu Met Gln Leu Trp Lys Asp Cys
             340                 345                 350
Thr Glu Val Lys Ser Thr Lys Ala Ser Ser Gly Gly Gln Arg Ser Ser
         355                 360                 365
Ser Gln Glu Pro Gln Pro Lys Asn Ser Pro Gln Ala Gly Gly Glu
         370                 375                 380
Tyr Glu Met Glu Thr Gly Gly Leu Pro Met Asp Leu Thr Asp Gly Ile
385                 390                 395                 400
Glu Lys Leu Arg Ala Asn Met Ser Ala Lys Tyr Asp Arg Ala Tyr Asn
                 405                 410                 415
Ile Leu His Ser Asp His Ser Val Thr Pro Gly Ser Pro Gly Leu Ser
                 420                 425                 430
Arg Arg Ser Ala Ser Ser Gly Gly Ser Gly Ser Ala Phe Ile Gln
             435                 440                 445
Leu Asp Pro Glu Val Gln Leu Pro Ser Gly Ser Gly Arg Ser Lys Arg
450                 455                 460
Gly Gln His Ser Ser Ala Arg Ser Leu Gly Asn Leu Asp Thr Val Glu
465                 470                 475                 480
Glu Asp Phe Pro Leu Glu Gln Glu Val Arg Asp Phe Lys Met Arg Arg
             485                 490                 495
Leu Ser Asp Tyr Val Pro Thr Pro Asp Leu Leu Glu Glu Thr Glu Pro
             500                 505                 510
Thr Gln Thr Pro Tyr Glu Arg Arg Ser Asn Pro Met Asp Lys Ile Thr
         515                 520                 525
Glu Thr Ile Gln Ser His Leu Lys Leu His Phe Asp Thr Pro Gly Val
         530                 535                 540
Pro Gln Ser Glu Ser Leu Ser His Leu Ala His Gly Met Thr Lys Ala
```

```
                  545                 550                 555                 560
Arg Ala Ala Arg Leu Phe Tyr Gln Ile Ala Val Leu Ala Thr Cys Asp
                565                 570                 575

Tyr Ile Lys Val Thr Gln Leu Glu Arg Lys Gly Asp Glu Leu Tyr Gly
                580                 585                 590

Asp Ile Leu Ile Ser Arg Gly Leu Lys Met
                595                 600

<210> SEQ ID NO 13
<211> LENGTH: 5860
<212> TYPE: DNA
<213> ORGANISM: Zea mays

<400> SEQUENCE: 13
cactgatgct cctggaactg cagtgacggt tcggccgtgt caaattctcg ggtgtagggt     60
gtacctctgg ccaagtgact gatattctga aaaacatacg gacttctagt ataggagaag    120
aggaatccta atcctagtaa ttatatctta gtagatatgt gcttagtctc ttgttaattt    180
tttgtcttga gaggactata tactgataa agtgataat ttattcagag aataaagaat      240
gggctccatg ctttgtctat gtattctctt cttgagggca atttacgcct cttgagaagg    300
gtggcttcgt tgttgggctc ttgaaggccc acgcagtcca acggagccca ctaagcctaa    360
ttctgtttct tcgcgatcga ttagctgatt agctccatgg cggcttcgaa aaaatcaaaa    420
taaaaaacta gcgccatggc ggggagggat aagaggcgac gagcggcgcc gctcgaaggc    480
gacgagcagc agttgcggcg gaggctggag gaagcggcgc tcctcctccg caggatcaaa    540
ggttttgtta ctcatctcct cgatcgcctg cccttaaatc ttccctctct cctgtagcgt    600
ctggagctga cgcgcggttg gggatggtgc agggcttgtg cgctggatcg tcgaagaggt    660
tgccgccggc cgctccccgt ctatagtgct ccaccggtac cggaactatt gctcctccgc    720
cgactctgcg tccccgtccc catggtttag cttccgcgcc cgctcccggg atcatctcct    780
tcccgaccaa ttcaccgtca catccctcga acaattttca cccaaatgtg tgacatccgt    840
agacctgggg cgcgcgctcg tgcgtgattg cagtgcctgc agctacgaca tcccgtcgg    900 cacggacgtc ctctctctgc tccacaagga ctaccacacc tcccgcctca gtacgaatac    960
atctaaatct ttgcatttat gtgatcacac taattacttt ctgatgcgtt gttcatgcgt   1020
agatgtgctc ctgagggtgc tgttcgtggt gcagcagctc ctgcagcaga caagcactg    1080 ctccaagagg gacatctact acatgtaccc ctccatcttc gtaggtctgt gctcagtagg   1140
tgcaatgttt gctcctcatt ccattatacg ggattactag aatttgcaca tatcttggct   1200
ccctgcagaa gtagcagttg ttgaccgtgc catcaacgat atctgcatac tcttcaagtg   1260
cagccggcac aatctcaacg tggtaggtcc ataggtgcca ctagtctgct gtcttccctg   1320
aagcttccat tgtgtattgt agaaaggact tgtgccatca acgatatttg ctccttcact   1380
aatatgcagc accatgacta ttacatactg tcttaatttc ataaccttt atctgactga    1440 atactgtgct cccttggctc tctgcaggtt cctgtagtga aagggtatga actgtcatag   1500
agttgaagct ctgaagatat gtccgtttgt tattcttcta ttattttaca acgcttcatt   1560
tttttataac ttaaataaac ccgttttttt tgttccttaa atcatcctgt gtgcttctca   1620
ccattatata agaaagatg atttggatgt gtttgatgag ctagtggggt tgggaacctg    1680
ggataccgtt ctttcaatgt agtcttagcc gtataggttt atgcatatga agaggaggaa   1740
gaaatgatgc catgatggat ctgttgttct tcccagtgtc agttcacaac tttgagatat   1800
```

```
atttttttttg atacagaaca tgtctgaatt catgaagagt tctctttggt ttatctgaat      1860
aaaaaatcaa tatagcataa gtgttaacta aattcactat aggaatttgg aaattctata      1920
tgatttccgt attacacttg ctgttacttg cattgttttt gctaggtttg cgatgttata      1980
ttcatagaac tatttgttat ttattcagtt gtttaattgt gtgcacatgt ctattccctt      2040
cattatccta gtttggtgat gggctggata agatttatgg agggcgaaaa gaaagtgtat      2100
tgtataacaa gcgtcaatgc tgtaagcttt tatgttctct gcccctaat tttgctaact       2160 ggtctattga taagatttca tttaatttgt ttgctttacc ttctgtatat tcaggctttc      2220
tccattcctg ttgacattga ggcaatcaaa ggttttttcca tcaactttag gaacacaacc     2280
cctttgtgct tttgtgaaat gtgtagaagg gaggggtag tgaaaaatca actctttcct       2340
tgatgttttg aagcacactg ggcaaaaagt cactgatcat ttttttgctct taaatggtac     2400 catagatctt caatttttttg tttcttttttt taaaagaaat tcataatctt acattctgaa    2460
ttaaataact actcccccctc ttccaagtta tagtttacta cttcactcta gctttgtccc    2520
aaatcaaacc tctctaactt cactttagtt atatgttttg ataagagaag atatccggtg     2580
cacatgaaag attggtgcac atggtgcaca tattaaatca tcaccactca atttagatct     2640
aacgtctcta gttgtttggt atattttgct aaggacaccc tccaacgtgg tggtgtgtag     2700
tgatggaagg tattatttgt aaattgaatg atcaactaaa gacgttagat ataaaataag    2760
tggtggtgat ttaatatgtg caccatatgc accagatatg tcctcttttg ataatgcatt    2820
tattgaactt ctaggtgata atatattgtt ctaaaacttg atcaaagtta gagaagtttg    2880
acttaggaca atgctaaagt gaagaattat ttgaaacatc gggagtacct tttatctttt    2940
ccagtcaaat tttgtaattg agatattata tggttgttta acaactcgga tttagacgtg   3000
cctacaccag tacacctcta tagcaaagct tttgatttcc tcccttgata ccctgaattg   3060
cattatagtg agctgaagtt gtcttattct ttcttctctt gcagatgttg ttagtgttgc   3120
ccactacata cttgtggttg agaaggagac aggtctttttt tttttttgcat ttaataattt  3180 ccgctctttg tacaatatgc ttcagtagtc cctttgcagt gttccagcgt ttggccaatg   3240
acaagttctg tgaaagaaat cgctgcattg ttattacagt aagtaacaac tctcacccga   3300
tgttatcaat tttcataatt ttttctctag tttcatgata ttgcattgtc aacccaggga   3360
agaggctatc cagatattcc aacaagaagg catgtgctct ttattcatta agttcctctt   3420
gcatatttct caaccgctat cccaattttta cattcttttt ccatcctaga ttcctgcggt   3480
accttgttga actgctgcat ctgcctgctt attgcttagt ggactcagat ccttatggtt   3540
tcgacattct ggctacctat aaatttggtt ccttggtagg catgatttat ctgatgctgc   3600
tatgctcatc tatatctatt gtctatgaac ttaacttcct tagcagattc acaggttaaa   3660
attgcaggta acgaatccat ggacatgatc atatactgca cctttcgtcc taaatcaaca   3720
gcttgtctgg cctctttgca tttgaaagtt ctattacttt atgaagtccc gttagcaata   3780
aggctgtgta ttagagcagt tcattttttcc cctcaaaata aacatgatta tgctcgtttt   3840
gctcatctta tcacaagcat gaccaaaata tttcttttttg ctctttgaaa cccaagatta   3900
tgacatattt acttgtgtta acttaccaac ctctgctact tgcgtaattt cattcttcaa   3960
gcaattggca catgatgcaa acttgttgcg tgtccctgat atacggtggc ttggagtttt   4020
cacatctgat tttgaagaat attgccttcc agactgctgc ctacttcgtt tgtcacctga   4080
aggtgaataa actgtagtga ttcaagtggc atacatactt tttttttggaa gatgttcctt    4140 agtttcttgt tgtatgtcaa atgccaacct gtgaaatcat gtgttctgct gcgcagatag    4200
```

```
gaggaaagct gaaggcattc ttgctaggtg ctatttacac agggaagccc cagaatggag    4260
gtaatgaagt aatgaaccag ctttggagtt ttactaggtg tattacaatt atatcctcca    4320
tgatatcatt gtgatctcca ggtcaagatc gaggtctatt agtgcatgga gttttactag    4380
agctttcgtg gaatctgatt tgtacagtca tcattcttat gatttagttg ctggagtttg    4440
agtttcttca gcaccagatc tttagcttca atgactgtat agcttcctgt ttttaccagt    4500
aaaggcacaa tagtttgaag cactttatat tttaagatat taaacgcatc atttcctatc    4560
aagaattctg agttatttt tacattttct ccctgaattt cacatgtatt ctctaatttg     4620
acaggtcaga gttggaagca atgctgcaaa agggtgtcaa gtttgagatt gaggcactat    4680
ccgcaaattc catttccttt ttatcgcatg agtacattcc ccagaaaatc aaacaaggca    4740
tgcatttata agattggaca ttcttgtatc cgtccaggat gtgtcataga gtacaatctt    4800
tttttgtctg attatagtta tatccggaga catatcatgt gcaaacacta aggatctgtt    4860
tcagaacata acataatatt tccttaatcc taagataata tcgtggtatt tgagcataac    4920 atgttattt agactaaaag atatttggga gcatatctaa aaactatgta ttttaaacca     4980
tggttttact aatactttt gtttgtacat aactacgtct tctcttctac actataactg     5040
aaatactgtg tttctaaacg aatgttggat tagactgata taaaatatac catatgtatg    5100
tcatgatata caataaactg tagtattata aactgtggtt ttaagaaaca gagtttccaa    5160
ataggcccca aggatgtgtt tggtttgatt atagttatat ctcgagacat atcatggatg    5220
tgtttggttt gaggacattc ctcacttttt ttatttgatt tgtggattag aatgagggca    5280
tgtttggttc tatgaggcta aactttagtc tctctttttt agtccttaaa ttacaaaaaa    5340
aaaggaccaa agaagagagg aaatctgatg tattacctt tagtccccaa tatttagtaa     5400
tttgaggagt aaaatgaaca accatcaagt tgatctatca ccatctcatc ctcacaagca    5460
acgtgccacc gtgaaactca tctgattatt atatatttat atgtcacagc tgcttccaac    5520
tactgctctc gcccattcct ggagcaggcg gcttgaacgg atgtaaagtt tttgttggta    5580
cttaattgat agtgcagtac gatggttcag gatggcgtaa aactaaaaca ggtaatggta    5640
gtagtaagta gcgttatgat cccccttagtt attttgtttc agcctgcagt tattttatat    5700
atgacctagt tagtttaaaa ctgaactgat taggtgcatc atatataaaa gaaaagagaa    5760
gcatatatat atatatatat ggctcacttt tgtggtatca gaaagcaaca ctgtttgtca    5820
gcataaaaga taacaaaagt agcgttattt tcccgccaga                          5860
```

<210> SEQ ID NO 14
<211> LENGTH: 1307
<212> TYPE: DNA
<213> ORGANISM: Zea mays

<400> SEQUENCE: 14

```
tcttcgcgat cgattagctg attagctcca tggcggcttc gaaaaaatca aaataaaaaa      60
ctagcgccat ggcggggagg gataagaggc gacgagcggc gccgctcgaa ggcgacgagc     120
agcagttgcg gcggaggctg gaggaagcgg cgctcctcct ccgcaggatc aaagggcttg    180
tgcgctggat cgtcgaagag gttgccgccg ccgctcccc gtctatagtg ctccaccggt     240
accggaacta ttgctcctcc gccgactctg cgtccccgtc cccatgtgcc tgcagctacg    300
acatccccgt cggcacggac gtcctctctc tgctccacaa ggactaccac acctcccgcc    360
tcagtacgaa tacatctaaa tctttgcatt tatgtgatca cactaattac tttctgatgc    420
```

| gttgttcatg cgtagatgtg ctcctgaggg tgctgttcgt ggtgcagcag ctcctgcagc | 480 |
| agaacaagca ctgctccaag agggacatct actacatgta ccctccatc ttcgtagaag | 540 |
| tagcagttgt tgaccgtgcc atcaacgata tctgcatact cttcaagtgc agccggcaca | 600 |
| atctcaacgt ggttcctgta gtgaaaggtt tggtgatggg ctggataaga tttatggagg | 660 |
| gcgaaaagaa agtgtattgt ataacaagcg tcaatgctgc tttctccatt cctgttgaca | 720 |
| ttgaggcaat caaagatgtt gttagtgttg cccactacat acttgtggtt gagaaggaga | 780 |
| caggtctttt ttttttttgtg ttccagcgtt tggccaatga caagttctgt gaaagaaatc | 840 |
| gctgcattgt tattacagga agaggctatc cagatattcc aacaagaaga ttcctgcggt | 900 |
| accttgttga actgctgcat ctgcctgctt attgcttagt ggactcagat ccttatggtt | 960 |
| tcgacattct ggctacctat aaatttggtt ccttgcaatt ggcacatgat gcaaacttgt | 1020 |
| tgcgtgtccc tgatatacgg tggcttggag ttttcacatc tgattttgaa gaatattgcc | 1080 |
| ttccagactg ctgcctactt cgtttgtcac ctgaagatag gaggaaagct gaaggcattc | 1140 |
| ttgctaggtg ctatttacac agggaagccc cagaatggag gtcagagttg gaagcaatgc | 1200 |
| tgcaaaaggg tgtcaagttt gagattgagg cactatccgc aaattccatt tccttttttat | 1260 |
| cgcatgagta cattccccag aaaatcaaac aaggcatgca tttataa | 1307 |

<210> SEQ ID NO 15
<211> LENGTH: 1239
<212> TYPE: DNA
<213> ORGANISM: Zea mays

<400> SEQUENCE: 15

| atggcgggga gggataagag gcgacgagcg gcgccgctcg aaggcgacga gcagcagttg | 60 |
| cggcggaggc tggaggaagc ggcgctcctc ctccgcagga tcaaagggct tgtgcgctgg | 120 |
| atcgtcgaag aggttgccgc cggccgctcc ccgtctatag tgctccaccg gtaccggaac | 180 |
| tattgctcct ccgccgactc tgcgtccccg tccccatgtg cctgcagcta cgacatcccc | 240 |
| gtcggcacgg acgtcctctc tctgctccac aaggactacc acacctcccg cctcagtacg | 300 |
| aatacatcta atctttgca tttatgtgat cacactaatt actttctgat gcgttgttca | 360 |
| tgcgtagatg tgctcctgag ggtgctgttc gtggtgcagc agctcctgca gcagaacaag | 420 |
| cactgctcca gagggacat ctactacatg taccccctcca tcttcgtaga agtagcagtt | 480 |
| gttgaccgtg ccatcaacga tatctgcata ctcttcaagt gcagccggca caatctcaac | 540 |
| gtggttcctg tagtgaaagg tttggtgatg gctggataa gatttatgga gggcgaaaag | 600 |
| aaagtgtatt gtataacaag cgtcaatgct gctttctcca ttcctgttga cattgaggca | 660 |
| atcaaagatt tgttagtgt tgcccactac atacttgtgg ttgagaagga gacaggtctt | 720 |
| ttttttttg tgttccagcg tttggccaat gacaagttct gtgaaagaaa tcgctgcatt | 780 |
| gttattacag gaagaggcta tccagatatt ccaacaagaa gattcctgcg gtaccttgtt | 840 |
| gaactgctgc atctgcctgc ttattgctta gtggactcag atccttatgg tttcgacatt | 900 |
| ctggctacct ataaatttgg ttccttgcaa ttggcacatg atgcaaactt gttgcgtgtc | 960 |
| cctgatatac ggtggcttgg agttttcaca tctgattttg aagaatattg ccttccagac | 1020 |
| tgctgcctac ttcgtttgtc acctgaagat aggaggaaag ctgaaggcat tcttgctagg | 1080 |
| tgctatttac acagggaagc cccagaatgg aggtcagagt tggaagcaat gctgcaaaag | 1140 |
| ggtgtcaagt ttgagattga ggcactatcc gcaaattcca tttccttttt atcgcatgag | 1200 |
| tacattcccc agaaaatcaa acaaggcatg catttataa | 1239 |

<210> SEQ ID NO 16
<211> LENGTH: 412
<212> TYPE: PRT
<213> ORGANISM: Zea mays

<400> SEQUENCE: 16

```
Met Ala Gly Arg Asp Lys Arg Arg Ala Ala Pro Leu Glu Gly Asp
1               5                   10                  15

Glu Gln Gln Leu Arg Arg Arg Leu Glu Ala Ala Leu Leu Leu Arg
                20                  25                  30

Arg Ile Lys Gly Leu Val Arg Trp Ile Val Glu Glu Val Ala Ala Gly
            35                  40                  45

Arg Ser Pro Ser Ile Val Leu His Arg Tyr Arg Asn Tyr Cys Ser Ser
        50                  55                  60

Ala Asp Ser Ala Ser Pro Ser Pro Cys Ala Cys Ser Tyr Asp Ile Pro
65                  70                  75                  80

Val Gly Thr Asp Val Leu Ser Leu Leu His Lys Asp Tyr His Thr Ser
                85                  90                  95

Arg Leu Ser Thr Asn Thr Ser Lys Ser Leu His Leu Cys Asp His Thr
            100                 105                 110

Asn Tyr Phe Leu Met Arg Cys Ser Cys Val Asp Val Leu Leu Arg Val
        115                 120                 125

Leu Phe Val Val Gln Gln Leu Leu Gln Gln Asn Lys His Cys Ser Lys
130                 135                 140

Arg Asp Ile Tyr Tyr Met Tyr Pro Ser Ile Phe Val Glu Val Ala Val
145                 150                 155                 160

Val Asp Arg Ala Ile Asn Asp Ile Cys Ile Leu Phe Lys Cys Ser Arg
                165                 170                 175

His Asn Leu Asn Val Val Pro Val Val Lys Gly Leu Val Met Gly Trp
            180                 185                 190

Ile Arg Phe Met Glu Gly Glu Lys Lys Val Tyr Cys Ile Thr Ser Val
        195                 200                 205

Asn Ala Ala Phe Ser Ile Pro Val Asp Ile Glu Ala Ile Lys Asp Val
    210                 215                 220

Val Ser Val Ala His Tyr Ile Leu Val Val Glu Lys Glu Thr Gly Leu
225                 230                 235                 240

Phe Phe Phe Val Phe Gln Arg Leu Ala Asn Asp Lys Phe Cys Glu Arg
                245                 250                 255

Asn Arg Cys Ile Val Ile Thr Gly Arg Gly Tyr Pro Asp Ile Pro Thr
            260                 265                 270

Arg Arg Phe Leu Arg Tyr Leu Val Glu Leu Leu His Leu Pro Ala Tyr
        275                 280                 285

Cys Leu Val Asp Ser Asp Pro Tyr Gly Phe Asp Ile Leu Ala Thr Tyr
    290                 295                 300

Lys Phe Gly Ser Leu Gln Leu Ala His Asp Ala Asn Leu Leu Arg Val
305                 310                 315                 320

Pro Asp Ile Arg Trp Leu Gly Val Phe Thr Ser Asp Phe Glu Glu Tyr
                325                 330                 335

Cys Leu Pro Asp Cys Cys Leu Leu Arg Leu Ser Pro Glu Asp Arg Arg
            340                 345                 350

Lys Ala Glu Gly Ile Leu Ala Arg Cys Tyr Leu His Arg Glu Ala Pro
        355                 360                 365

Glu Trp Arg Ser Glu Leu Glu Ala Met Leu Gln Lys Gly Val Lys Phe
```

```
                    370               375               380
            Glu Ile Glu Ala Leu Ser Ala Asn Ser Ile Ser Phe Leu Ser His Glu
            385                 390                 395                 400

Tyr Ile Pro Gln Lys Ile Lys Gln Gly Met His Leu
                        405                 410
```

<210> SEQ ID NO 17
<211> LENGTH: 21
<212> TYPE: DNA
<213> ORGANISM: Zea mays

<400> SEQUENCE: 17
ttctcctcct ctcaattgcc t                                            21

<210> SEQ ID NO 18
<211> LENGTH: 21
<212> TYPE: DNA
<213> ORGANISM: Zea mays

<400> SEQUENCE: 18
tcaccatctt ttcaatctgc t                                            21

<210> SEQ ID NO 19
<211> LENGTH: 600
<212> TYPE: DNA
<213> ORGANISM: Zea mays

<400> SEQUENCE: 19
tccatccagc tccaggcgtt ccagaggccc tgatacagga gatgttccag cacaacccag    60
gggtgtccag ggagggtctc ggcctgtaca taagccagaa gctggtgaaa cgatgagcg    120 gcacgttgca gtacctacga gaagccgaca cctcttcgtt catcatcctg atagagttcc    180
cggtcgccca gctcagcagc aagcggtcca agccttcgcc aagtaaattc tgacactgat    240
gctcctggaa ctgcagtgac ggttcggccg tgtcaaattc tcgggtgtag ggtgtacctc    300
tggccaagtg actgatattc tgaaaaacat acggacttct agtataggag aagaggaatc    360
ctaatcctag taattatatc ttagtagata tgtgcttagt ctcttgttaa ttttttgtct    420
tgagaggact atatactg ataaagtgat aatttattca gagaataaag aatgggctcc    480
atgctttgtc tatgtattct cttcttgagg gcaatttacg cctcttgaga agggtggctt    540 cgttgtttggg ctcttgaagg cccacgcagt ccaacggagc ccactaagcc taattctgtt    600

<210> SEQ ID NO 20
<211> LENGTH: 600
<212> TYPE: DNA
<213> ORGANISM: Zea mays

<400> SEQUENCE: 20
ttacaatcga agacgagctc gcatcgtggc aacaaatttt ggtgctccaa agctttggaa    60
aggttatcct caacattgtt gggatccatg gcggtctaga atcaaccata tgaaacacta    120
gcggctaggg ttcggaggag atcattaggg aggagaagga gaggtcaagt ctaagttggg    180
ctaggtgaga acgatcatgg gtagatggat ggcagtaccg ggtaattttc atcaacttac    240
gattaatagt gggtctttta ttaaaaataa gctgatataa gcatcttttg agaagcttat    300
agggttatca taatctcaag tactagatta tataatttta tcacataagt tgcttcatac    360
ttagtttgtc tatcactagc ttatttacat agaatttaga ttatataata ccaacccta    420 aatgacctga accaaagata cccagattgc ttcacatcat ttgtgtggca ctgtggctac    480

```
atgaggacgt gggaatgggc gaatggcgcg gaacgacccc cgataggttt ccgatattgc    540
cctccccacg cgcacgattt aaccgatccg cccccgtttc tttcttttc tccacgagaa    600
```

<210> SEQ ID NO 21
<211> LENGTH: 600
<212> TYPE: DNA
<213> ORGANISM: Zea mays

<400> SEQUENCE: 21

```
tattcaaatt ctactccgta aatagtgcag cacacgacac aaaatagtgt tttgggtaat     60
gaaatgctgg agacggtccg aatgtcgacc gaagcttttc agacatgctc gctccaaatt    120
taggtcagct gtctctaatc tgtgactgcg cgctacgggt acgtaaattt tgtagtagca    180
gaacgctaaa tctctttcga atcactgttt ttattatgtc gagcaaaaaa aacatagctt    240
cgtcgtgaat tttgaattat aaatgatcag cgagaatatt tcagctgaat taaaatgtcc    300
tatacagaca agaaagcctt aaatttcgga tgctgggaac ggtatccgcc gctgatcatc    360
ctgaggagta atatagcata ataattaaaa ttattaagct tccaacgccg atgccaacgg    420
tcagaaagtt cgaaatcatt gtgctacatg aacctggtgt accatcctgc ccgtccatca    480
ctcttgatct gaatggaatg tccgcatgcc gctctcggcc caccatacac cgagcccttc    540
ggtcgtcgcc agttttgaat ttcgaacatg ttaaaagccc cgcctgcgct gccaccacc    600
```

<210> SEQ ID NO 22
<211> LENGTH: 600
<212> TYPE: DNA
<213> ORGANISM: Zea mays

<400> SEQUENCE: 22

```
cttaaaatat ttcacattat ccaaaggact tgtatgaaag tagaagtatt cgaattcgat     60
ccatataaaa gggttgagat ctggtccgta tctgaatccg gtattcagta tctaatctgt    120
acctattata tatctgtatc cgtaataaaa attgaatatt taagatgttg atatttattt    180
aatatttatc caacacaatt tgataatatc cgtattaaat ctaaatgcaa ataaaaaata    240
aatataaata taaacgagta ataccctatta catacctctc cgcacgggca actgtccaaa    300
aattcgaaat tcatatatca taccacgcca cgccgcgatc tcgatccacc aaccgcgctg    360
tataccggcg taccggcccg ctgttcggtg tccgcgaatg ccatttcaga cccacaattt    420
cgtttcgact gcacgcgctt ggtccataca ccggatccat cactgcccgt tggccgttgc    480
acttcgccac acgaacgtcc agatgtgact cggggtccac caaaggcacc gtacacggta    540
caccggttat ctctccttcg ccatttcaaa taggtttaaa catcccgctc aatagccgga    600
```

METHODS AND COMPOSITIONS FOR PRODUCING CLONAL, NON-REDUCED, NON-RECOMBINED GAMETES

CROSS REFERENCE TO RELATED APPLICATIONS

This patent application is a 371 National Stage Entry of PCT patent application No. PCT/US2017/022962, filed on Mar. 17, 2017, which claims the benefit of and priority to U.S. Provisional Application No. 62/310,006, filed Mar. 18, 2016, the entire contents of each is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "7113WOPCT_SequenceListing" created on Mar. 9, 2017, and having a size of 69 kilobytes and is filed concurrently with the specification. The sequence listing contained in this ASCII formatted document is part of the specification and is herein incorporated by reference in its entirety.

FIELD OF THE INVENTION

The field relates to apomixis and molecular biology.

BACKGROUND

Sexual reproduction increases genetic diversity and is based on meiosis and fertilization. Meiosis has two meiotic germ cell divisions, meiosis I and meiosis II. During the first division (meiosis I), paternal and maternal chromosomes are able to cross-over and exchange genes before the pairs of chromosomes are separated into two haploid cells. Each resulting haploid cell contains only half the number of chromosomes and two chromatid pairs. The second meiotic division (meiosis II) segregates the sister chromatids and results in the formation of four haploid gametes. A gamete from a male and female parent can unite to form a genetically unique diploid zygote.

In contrast, asexual reproduction does not involve the union of gametes. In some examples, asexual reproduction in plants can be achieved by avoiding meiosis. The avoidance of meiosis could allow for a parent plant to produce gametes that are genetically identical to itself.

SUMMARY

One embodiment of the current disclosure is a method of obtaining a maize plant that produces clonal, non-reduced, non-recombined gametes by suppressing in the maize plant the activity of an endogenous Spo11 polynucleotide or polypeptide, an endogenous Rec8 (aka Afd1 in maize) polynucleotide or polypeptide, an endogenous OSD1-1A polynucleotide or polypeptide, and an endogenous OSD1-3A polynucleotide or polypeptide. Accordingly, one embodiment is a maize plant that produces clonal, non-reduced, non-recombined gametes, where the maize plant comprises suppressed activity of an endogenous Spo11 polynucleotide or polypeptide, an endogenous Rec8 polynucleotide or polypeptide, an endogenous OSD1-1A polynucleotide or polypeptide, and an endogenous OSD1-3A polynucleotide or polypeptide. In some embodiments, the Spo11 polynucleotide is selected from the group consisting of: a polynucleotide that encodes the polypeptide of SEQ ID NO:16; a polynucleotide comprising the sequence set forth in SEQ ID NO:13, 14, 15, or 19; and a polynucleotide having at least 80% sequence identity to SEQ ID NO: 13, 14, 15, or 19 and the Spo11 polypeptide is selected from the group consisting of: a polypeptide comprising SEQ ID NO: 16; a polypeptide that is at least 80% identical to the amino acid sequence of SEQ ID NO:16; a polypeptide that is encoded by a nucleic acid molecule comprising a nucleotide sequence that is at least 80% identical to the sequence set forth in SEQ ID NO:13, 14 or 15. In some embodiments, the Rec8 polynucleotide is selected from the group consisting of: a polynucleotide that encodes the polypeptide of SEQ ID NO:12, a polynucleotide comprising the sequence set forth in SEQ ID NO:9, 10, 11 or 20; and a polynucleotide having at least 80% sequence identity to SEQ ID NO:9, 10, 11 or 20; and the Rec8 polypeptide is selected from the group consisting of: a polypeptide comprising SEQ ID NO: 12; a polypeptide that is at least 80% identical to the amino acid sequence of SEQ ID NO:12; a polypeptide that is encoded by a nucleic acid molecule comprising a nucleotide sequence that is at least 80% identical to the sequence set forth in SEQ ID NO:9, 10 or 11. In some embodiments, the endogenous OSD1-1A polynucleotide or polypeptide is selected from the group consisting of: a polynucleotide that encodes the polypeptide of SEQ ID NO:4; a polynucleotide comprising the sequence set forth in SEQ ID NO:1, 2, 3 or 21; and a polynucleotide having at least 80% sequence identity to the sequence set forth in SEQ ID NO: 1, 2, 3, or 21; and the OSD1-1A polypeptide is selected from the group consisting of: a polypeptide comprising SEQ ID NO:4; a polypeptide that is at least 80% identical to the amino acid sequence of SEQ ID NO:4; a polypeptide that is encoded by a nucleic acid molecule comprising a nucleotide sequence that is at least 80% identical to the sequence set forth in SEQ ID NO:1, 2 or 3. In some embodiments, the endogenous OSD1-3A polynucleotide is selected from the group consisting of: a polynucleotide that encodes the polypeptide of SEQ ID NO:8; a polynucleotide comprising the sequence set forth in SEQ ID NO:5, 6, 7, or 22; and a polynucleotide having at least 80% sequence identity to the sequence set forth in SEQ ID NO:5, 6, 7, or 22, and the OSD1-3A polypeptide is selected from the group consisting of: a polypeptide comprising SEQ ID NO:8; a polypeptide that is at least 80% identical to the amino acid sequence of SEQ ID NO:8; a polypeptide that is encoded by a nucleic acid molecule comprising a nucleotide sequence that is at least 80% identical to the sequence set forth in SEQ ID NO: 5, 6, or 7.

In certain embodiments, the activity of the endogenous Spo11 polynucleotide or polypeptide, Rec8 polynucleotide or polypeptide, OSD1-1A polynucleotide or polypeptide, and/or OSD1-3A polynucleotide or polypeptide, or combinations thereof is suppressed using genome editing. In certain embodiments the suppression is a knock-out of the gene. In some approaches, the suppression results from a nucleotide modification of one or more the endogenous Spo11, Rec8, OSD1-1A or OSD1-3A polynucleotide sequences. In some embodiments, the nucleotide modification is a deletion, addition, or substitution of one or more nucleotides. In certain embodiments, the suppression results from an amino modification of one or more the endogenous Spo11, Rec8, OSD1-1A or OSD1-3A polypeptide sequences. In some embodiments, the amino acid modification is a deletion, addition, or substitution of one or more amino acids. In certain embodiments, the maize plant is a hybrid. In some embodiments, the activity of the endogenous Spo11 polynucleotide or polypeptide, Rec8 polynucleotide or polypeptide, OSD1-1A polynucleotide or polypeptide, OSD1-3A polynucleotide or polypeptide, or combinations thereof is suppressed using RNA-based silencing approaches, for example, antisense, microRNA, RNAi, or hairpin molecule, described elsewhere herein. In certain embodiments, the maize plant is a hybrid. In certain embodiments, the maize plant is an inbred. In certain embodiments, the maize plant is a female or male parent. Gametes obtained from this plant may be clonal, non-reduced, non-recombined gametes.

One embodiment of the disclosure includes a method of obtaining a maize plant that produces clonal, non-reduced, non-recombined gametes by crossing maize plants that are heterozygous or homozygous for the suppressed endogenous Spo11, Rec8, OSD1-1A and OSD1-3A activity with one another until a maize plant is obtained that is homozygous for the suppressed endogenous Spo11, Rec8, OSD1-1A and OSD1-3A activity. In certain embodiments, the maize plant is a hybrid. In certain embodiments, the maize plant is an inbred. In certain embodiments, the maize plant is a female or male parent. Gametes obtained from this plant may be clonal, non-reduced, non-recombined gametes.

In certain embodiments, the disclosure includes a method for obtaining a maize plant with a modified endogenous Spo11 polynucleotide sequence. In certain aspects, the modified endogenous Spo11 disrupts the homologous pairing and subsequent recombination of chromosomes during meiosis in plants. In certain aspects, the activity of the endogenous Spo11 polynucleotide or polypeptide is suppressed using genome editing approaches, for example, by genetically modifying the endogenous Spo11. In some approaches, the suppression results from a nucleotide modification of the endogenous maize Spo11 polynucleotide sequences. In some embodiments, the nucleotide modification is a deletion, addition, or substitution of one or more nucleotides. In certain embodiments, the suppression results from an amino acid modification of the endogenous Spo11 polypeptide sequence. In some embodiments, the amino acid modification is a deletion, addition, or substitution of one or more amino acids. In certain aspects, the activity of the endogenous Spo11 polynucleotide or polypeptide is suppressed using RNA-based silencing approaches, for example, antisense, microRNA, RNAi, or hairpin molecule, described elsewhere herein. In certain embodiments, the suppression of Spo11 is a knock-out of the gene.

In certain embodiments, the disclosure includes a method for obtaining a maize plant with a modified endogenous Rec8 polynucleotide sequence. In certain aspects, the modified endogenous Rec8 disrupts the orientation of kinetochores and subsequent random distribution of chromatids during meiosis II in a plant cell. In certain aspects, the activity of the endogenous Rec8 polynucleotide or polypeptide is suppressed using genome editing approaches, for example, by genetically modifying the endogenous Rec8. In some approaches, the suppression results from a nucleotide modification of the endogenous maize Rec8 polynucleotide sequences. In some embodiments, the nucleotide modification is a deletion, addition, or substitution of one or more nucleotides. In certain embodiments, the suppression results from an amino acid modification of the endogenous Rec8 polypeptide sequence. In some embodiments, the amino acid modification is a deletion, addition, or substitution of one or more amino acids. In certain aspects, the activity of the endogenous Rec8 polynucleotide or polypeptide is suppressed using RNA-based silencing approaches, for example, antisense, microRNA, RNAi, or hairpin molecule, described elsewhere herein. In certain embodiments, the suppression of Rec8 is a knock-out of the gene.

In certain embodiments, the disclosure includes a method for obtaining a maize plant with a modified endogenous OSD1-1A polynucleotide sequence. In certain aspects, the modified endogenous OSD1-1A and modified endogenous OSD1-3A together disrupt the progression of meiosis II division in a plant cell and produce non-reduced gametes. In certain aspects, the activity of the endogenous OSD1-1A polynucleotide or polypeptide is suppressed using genome editing approaches, for example, by genetically modifying the endogenous Rec8. In some approaches, the suppression results from a nucleotide modification of one or more the endogenous maize OSD1-1A polynucleotide sequences. In some embodiments, the nucleotide modification is a deletion, addition, or substitution of one or more nucleotides. In certain embodiments, the suppression results from an amino acid modification of the endogenous OSD1-1A polypeptide sequence. In some embodiments, the amino acid modification is a deletion, addition, or substitution of one or more amino acids. In certain aspects, the activity of the endogenous OSD1-1A polynucleotide or polypeptide is suppressed using RNA-based silencing approaches, for example, antisense, microRNA, RNAi, or hairpin molecule, described elsewhere herein. In certain embodiments, the suppression of OSD1-1A is a knock-out of the gene.

In certain embodiments, the disclosure includes a method for obtaining a maize plant with a modified endogenous OSD1-3A polynucleotide sequence. In certain aspects, the modified endogenous OSD1-1A and the modified endogenous OSD1-3A together disrupt the progression of meiosis II division in a plant cell and produce non-reduced gametes. In certain aspects, the activity of the endogenous OSD1-3A polynucleotide or polypeptide is suppressed using genome editing approaches, for example, by genetically modifying the endogenous Rec8. In some approaches, the suppression results from a nucleotide modification of one or more the endogenous maize OSD1-3A polynucleotide sequences. In some embodiments, the nucleotide modification is a deletion, addition, or substitution of one or more nucleotides. In certain embodiments, the suppression results from an amino acid modification of the endogenous OSD1-3A polypeptide sequence. In some embodiments, the amino acid modification is a deletion, addition, or substitution of one or more amino acids. In certain aspects, the activity of the endogenous OSD1-3A polynucleotide or polypeptide is suppressed using RNA-based silencing approaches, for example, antisense, microRNA, RNAi, or hairpin molecule, described elsewhere herein. In certain embodiments, the suppression of OSD1-3A is a knock-out of the gene.

BRIEF DESCRIPTION OF THE SEQUENCE LISTING

The disclosure can be more fully understood from the following detailed description and the accompanying Sequence Listing which form a part of this application.

Table 1 presents SEQ ID NOs for the Spo11, Rec8, OSD1-1A, OSD1-3A polynucleotide and polypeptide sequences from *Zea mays* and maize OSD1-1A and OSD1-3A amiRNA target sequences. It is understood, as those skilled in the art will appreciate, that the disclosure encompasses more than these specific exemplary sequences.

TABLE 1

| Plant | Sequence Name | SEQ ID NO: |
|---|---|---|
| maize | OSD1-1A genomic DNA | 1 |
| maize | OSD1-1A cDNA | 2 |
| maize | OSD1-1A CDS (coding) | 3 |
| maize | OSD1-1A amino acid | 4 |
| maize | OSD1-3A genomic DNA | 5 |
| maize | OSD1-3A cDNA | 6 |
| maize | OSD1-3A CDS (coding) | 7 |
| maize | OSD1-3A amino acid | 8 |
| maize | Rec8 genomic DNA | 9 |
| maize | Rec8 cDNA | 10 |
| maize | Rec8 CDS (coding) | 11 |
| maize | Rec8 amino acid | 12 |
| maize | Spo11 genomic DNA | 13 |
| maize | Spo11 cDNA | 14 |
| maize | Spo11 CDS (coding) | 15 |
| maize | Spo11 amino acid | 16 |
| maize | OSD1-1A amiRNA target sequence | 17 |
| maize | OSD1-3A amiRNA target sequence | 18 |
| maize | Spo11 upstream sequence | 19 |
| maize | Rec8 upstream sequence | 20 |
| maize | OSD1-1A upstream sequence | 21 |
| maize | OSD1-3A upstream sequence | 22 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise.

In describing the present invention, the following terms will be employed, and are intended to be defined as indicated below.

The terms "altered target site", "altered target sequence", "modified target site", and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii). Also, multiple mutations could be used in combination.

"Antisense inhibition" generally refers to the production of antisense RNA transcripts capable of suppressing the expression of the target gene or gene product. "Antisense RNA" generally refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

The terms "artificial target site" and "artificial target sequence" are used interchangeably herein and refer to a target sequence that has been introduced into the genome of a cell or organism. Such an artificial target sequence can be identical in sequence to an endogenous or native target sequence in the genome of a cell but be located in a different position (i.e., a non-endogenous or non-native position) in the genome of a cell or organism.

"Coding region" generally refers to the portion of a messenger RNA (or the corresponding portion of another nucleic acid molecule such as a DNA molecule) which encodes a protein or polypeptide. "Non-coding region" generally refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

"Cosuppression" generally refers to the production of sense RNA transcripts capable of suppressing the expression of the target gene or gene product. "Sense" RNA generally refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

"Developmentally regulated promoter" generally refers to a promoter whose activity is determined by developmental events.

The terms "dicot" and "dicotyledonous plant" are used interchangeably herein. A dicot of the current disclosure includes the following families: Brassicaceae, Leguminosae, and Solanaceae.

"Expression" generally refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

The terms "full complement" and "full-length complement" are used interchangeably herein, and refer to a complement of a given nucleotide sequence, wherein the complement and the nucleotide sequence consist of the same number of nucleotides and are 100% complementary.

"Gamete" refers to a reproductive cell having the 1 n set (haploid number) of chromosomes that can fuse with another gamete of the opposite sex during fertilization in organisms undergoing sexual reproduction. As used herein, a gamete in organisms undergoing asexual reproduction refers to a cell having a 2n number (an unreduced number) of chromosomes.

"Genome" as it applies to plant cells encompasses not only chromosomal DNA found within the nucleus, but organelle DNA found within subcellular components (e.g., mitochondrial, plastid) of the cell.

"Heterologous" with respect to sequence means a sequence that originates from a foreign species, or, if from the same species, is substantially modified from its native form in composition and/or genomic locus by deliberate human intervention.

The term "introduced" in the context of inserting a nucleic acid into a cell, means "transfection" or "transformation" or "transduction" and includes reference to the incorporation of a nucleic acid or nucleic acid fragment into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

"Isolated" generally refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. The term also embraces recombinant polynucleotides and chemically synthesized polynucleotides.

The terms "miRNA-star sequence" and "miRNA* sequence" are used interchangeably herein and they refer to a sequence in the miRNA precursor that is highly complementary to the miRNA sequence. The miRNA and miRNA* sequences form part of the stem region of the miRNA precursor hairpin structure.

The terms "monocot" and "monocotyledonous plant" are used interchangeably herein. A monocot of the current disclosure includes the Gramineae.

As used herein, "nucleic acid" includes reference to a deoxyribonucleotide or ribonucleotide polymer in either single- or double-stranded form.

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. In certain embodiments, sequence identity may be based on the Clustal V or Clustal W method of alignment. The term "about" when used herein in context with percent sequence identity means +/−1.0%.

"Phenotype" means the detectable characteristics of a cell or organism.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Sorghum, Avena, Hordeum, Secale, Allium* and *Triticum*. A particularly preferred plant is *Zea mays*.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

"Polypeptide", "peptide", "amino acid sequence" and "protein" are used interchangeably herein to refer to a polymer of amino acid residues.

"Promoter functional in a plant" is a promoter capable of controlling transcription in plant cells whether or not its origin is from a plant cell.

As used herein "promoter" includes reference to a region of DNA upstream from the start of transcription and involved in recognition and binding of RNA polymerase and other proteins to initiate transcription.

A "plant promoter" is a promoter capable of initiating transcription in plant cells.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Recombinant" generally refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" generally refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" means conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence. The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

"Silencing," as used herein with respect to a target gene, refers generally to the suppression of levels of mRNA or protein/enzyme expressed by the target gene, and/or the level of the enzyme activity or protein functionality.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

"Suppression DNA construct" is a recombinant DNA construct which when transformed or stably integrated into the genome of the plant, results in "silencing" of a target gene in the plant. The target gene may be endogenous or transgenic to the plant.

The terms "suppress", "suppressed", "suppression", "suppressing" and "silencing", are used interchangeably herein and include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches and the like.

The terms "target site", "target sequence", "target DNA", "target locus", "genomic target site", "genomic target sequence", and "genomic target locus" are used interchangeably herein and refer to a polynucleotide sequence in the genome (including chloroplast and mitochondrial DNA) of a cell at which a double-strand break is induced in the cell genome. The target site can be an endogenous site in the genome of a cell or organism, or alternatively, the target site can be heterologous to the cell or organism and thereby not be naturally occurring in the genome, or the target site can be found in a heterologous genomic location compared to where it occurs in nature. As used herein, terms "endogenous target sequence" and "native target sequence" are used interchangeably herein to refer to a target sequence that is endogenous or native to the genome of a cell or organism and is at the endogenous or native position of that target sequence in the genome of a cell or organism. Cells include plant cells as well as plants and seeds produced by the methods described herein.

"Tissue-specific promoter" and "tissue-preferred promoter" are used interchangeably, and refer to a promoter that is expressed predominantly but not necessarily exclusively in one tissue or organ, but that may also be expressed in one specific cell.

"Transgenic" generally refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transgenic plant" includes reference to a plant which comprises within its genome a heterologous polynucleotide.

"Transgenic plant" also includes reference to plants which comprise more than one heterologous polynucleotide within their genome. Each heterologous polynucleotide may confer a different trait to the transgenic plant.

"Transcription terminator", "termination sequences", or "terminator" refer to DNA sequences located downstream of a protein-coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" generally refers to a polynucleotide sequence that, when operably linked to the 3' end of a second polynucleotide sequence that is to be expressed, is capable of terminating transcription from the second polynucleotide sequence and facilitating efficient 3' end processing of the messenger RNA resulting in addition of poly A tail. Transcription termination is the process by which RNA synthesis by RNA polymerase is stopped and both the processed messenger RNA and the enzyme are released from the DNA template.

The term "under stringent conditions" means that two sequences hybridize under moderately or highly stringent conditions.

The term "univalent" means that a chromosome that is not paired with its homologous chromosome during synapsis.

The term "bivalents" means that two homologous chromosomes paired at meiosis I.

INTRODUCTION

Described herein are maize Spo11, Rec8, OSD1-1 and OSD1-3 polynucleotides and polypeptides. The term "Spo11 polypeptide" refers to one or more Spo11 amino acid sequences. The term is also inclusive of fragments, variants, homologs, alleles or precursors (e.g., preproproteins or proproteins) thereof. A "Spo11 protein" comprises a Spo11 polypeptide. Unless otherwise stated, the term "Spo11 nucleic acid" means a nucleic acid comprising a polynucleotide ("Spo11 polynucleotide") encoding a Spo11 polypeptide. As used herein, Spo11 activity refers to the Spo11 protein's ability to promote homologous pairing and double strand breaks (DSBs) that result in recombination between homologous chromosomes during meiosis in plants. As shown in Example 1, a maize spo11 mutant resulted in the formation of univalent rather than bivalents at meiosis I, which indicates that Spo11 is involved in homologous pairing of chromosomes during meiosis.

The term "Rec8 polypeptide" refers to one or more Rec8 amino acid sequences. The term is also inclusive of fragments, variants, homologs, alleles or precursors (e.g., preproproteins or proproteins) thereof. A "Rec8 protein" comprises a Rec8 polypeptide. Unless otherwise stated, the term "Rec8 nucleic acid" means a nucleic acid comprising a polynucleotide ("Rec8 polynucleotide") encoding a Rec8 polypeptide. The terms Rec8 and Afd1 used herein interchangeably. As described in Example 1, a maize Rec8 mutant showed chromosome disorientation at meiosis I, resulting in unbalanced meiotic products at meiosis II. As used herein, Rec8 activity refers to the Rec8 protein's ability to bind sister chromatids of homologous chromosomes for proper separation during meiosis 1 and to orient kinetochores during meiosis in plants.

When maize was disrupted for both spo11/rec8 the double mutant had a mitotic like first division, rather than a meiosis division. See, for example, Example 1.

The term "OSD1-1A polypeptide" refers to one or more OSD1-1A amino acid sequences. The term is also inclusive of fragments, variants, homologs, alleles or precursors (e.g., preproproteins or proproteins) thereof. A "OSD1-1A protein" comprises a OSD1-1A polypeptide. Unless otherwise stated, the term "OSD1-1A nucleic acid" means a nucleic acid comprising a polynucleotide ("OSD1-1A polynucleotide") encoding a OSD1-1A polypeptide. As used herein, OSD1-1A activity refers to the OSD1-1A protein's ability to promote the progression of meiosis II division during meiosis in plants and produce reduced gametes.

The term "OSD1-3A polypeptide" refers to one or more OSD1-3A amino acid sequences. The term is also inclusive of fragments, variants, homologs, alleles or precursors (e.g., preproproteins or proproteins) thereof. A "OSD1-3A protein" comprises a OSD1-3A polypeptide. Unless otherwise stated, the term "OSD1-3A nucleic acid" means a nucleic acid comprising a polynucleotide ("OSD1-3 polynucleotide") encoding a OSD1-3A polypeptide. As used herein, OSD1-3A activity refers to the OSD1-3A protein's ability to promote the progression of meiosis II division during meiosis in plants and produce reduced gametes. Suppression of both OSD1-1A and OSD1-3A together in maize may result in the early exit of meiosis and non-reduced gametes. In species other than maize, suppression of one OSD1 gene may be sufficient to disrupt meiosis and reduction of gametes, for example, in rice. Use of amiRNA for both maize OSD1-1A and OSD1-3A in the maize rec8/spo11 mutant described in Example 1 resulted in the production of both male and female reduced and non-reduced gametes, indicating a role for maize OSD1-1A and OSD1-3A together in meiosis II division.

The suppression of Spo11, Rec8, OSD1-1A, and OSD1-3A polynucleotides and polypeptides or combinations thereof thus provide an opportunity to manipulate sexual reproduction and/or alter gametophyte and seed development. Suppression of Spo11, Rec8 and OSD1-1A, and OSD1-3A polynucleotides and polypeptides or combinations thereof may be used to produce clonal, non-reduced and non-recombined male and/or female gametes. In certain embodiments, the methods include suppressing an endogenous Spo11, Rec8 and OSD1-1A, and OSD1-3A polynucleotides and polypeptides or combinations thereof in a plant or plant cell. In certain embodiments, the plant cell is a microspore mother cell (which gives rise to haploid microspores), megaspore mother cell (which gives rise to a haploid megaspore) or any other plant cell where the gene, e.g. Spo11, Rec8 and OSD1-1A, and OSD1-3A, is expressed. Embodiments include isolated polynucleotides and polypeptides, recombinant DNA constructs useful for modifying meiosis in plant cells, asexual reproductive development and/or producing clonal progeny, including seeds and plants, that are non-reduced and non-recombined with respect to gametes.

The present disclosure includes the following isolated polynucleotides and polypeptides:

An isolated Spo11 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:16; or (ii) a full complement of the nucleic acid sequence of (i), wherein the full complement and the nucleic acid sequence of (i) consist of the same number of nucleotides and are 100% complementary.

An isolated Spo11 polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:16.

An isolated Spo11 polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO:13, 14, 15, or 19 and combinations thereof; or (ii) a full complement of the nucleic acid sequence of (i).

An isolated Spo11 polynucleotide comprising a nucleotide sequence, wherein the nucleotide sequence is hybridizable under stringent conditions with a DNA molecule comprising the full complement of SEQ ID NO:13, 14, 15, or 19. The isolated Spo11 protein of the present disclosure may also be a protein which is encoded by a nucleic acid comprising a nucleotide sequence hybridizable under stringent conditions with the complementary strand of the nucleotide sequence of SEQ ID NO:13, 14, or 15.

An isolated Spo11 polynucleotide comprising a nucleotide sequence, wherein the nucleotide sequence is derived from SEQ ID NO:13, 14, 15, or 19 by alteration of one or more nucleotides by at least one method selected from the group consisting of: deletion, substitution, addition and insertion.

An isolated Spo11 polynucleotide comprising a nucleotide sequence, wherein the nucleotide sequence corresponds to an allele of SEQ ID NO:13, 14, 15, or 19.

Any of the foregoing isolated polynucleotides may be utilized in any recombinant DNA constructs (including suppression DNA constructs) of the present disclosure.

An isolated Rec8 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:12; or (ii) a full complement of the nucleic acid sequence of (i), wherein the full complement and the nucleic acid sequence of (i) consist of the same number of nucleotides and are 100% complementary.

An isolated Rec8 polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:12.

An isolated Rec8 polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO:9, 10, 11 or 20 and combinations thereof; or (ii) a full complement of the nucleic acid sequence of (i).

An isolated Rec8 polynucleotide comprising a nucleotide sequence, wherein the nucleotide sequence is hybridizable under stringent conditions with a DNA molecule comprising the full complement of SEQ ID NO:9, 10, 11 or 20. The isolated Rec8 protein of the present disclosure may also be a protein which is encoded by a nucleic acid comprising a nucleotide sequence hybridizable under stringent conditions with the complementary strand of the nucleotide sequence of SEQ ID NO: 9, 10, or 11.

An isolated Rec8 polynucleotide comprising a nucleotide sequence, wherein the nucleotide sequence is derived from SEQ ID NO: 9, 10, 11 or 20 by alteration of one or more nucleotides by at least one method selected from the group consisting of: deletion, substitution, addition and insertion.

An isolated Rec8 polynucleotide comprising a nucleotide sequence, wherein the nucleotide sequence corresponds to an allele of SEQ ID NO:9, 10, 11 or 20.

Any of the foregoing isolated polynucleotides may be utilized in any recombinant DNA constructs (including suppression DNA constructs) of the present disclosure.

An isolated OSD1-1 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:4; or (ii) a full complement of the nucleic acid sequence of (i), wherein the full complement and the nucleic acid sequence of (i) consist of the same number of nucleotides and are 100% complementary.

An isolated OSD1-1A polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:4.

An isolated OSD1-1A polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO:1, 2, 3 or 21 and combinations thereof; or (ii) a full complement of the nucleic acid sequence of (i). Any of the foregoing isolated polynucleotides may be utilized in any recombinant DNA constructs (including suppression DNA constructs) of the present disclosure.

An isolated OSD1-1A polynucleotide comprising a nucleotide sequence, wherein the nucleotide sequence is hybridizable under stringent conditions with a DNA molecule comprising the full complement of SEQ ID NO:1, 2, 3 or 21. The isolated OSD1-1A protein of the present disclosure may also be a protein which is encoded by a nucleic acid comprising a nucleotide sequence hybridizable under stringent conditions with the complementary strand of the nucleotide sequence of SEQ ID NO:1, 2, or 3.

An isolated OSD1-1A polynucleotide comprising a nucleotide sequence, wherein the nucleotide sequence is derived from SEQ ID NO:1, 2, 3 or 21 by alteration of one or more nucleotides by at least one method selected from the group consisting of: deletion, substitution, addition and insertion.

An isolated OSD1-1A polynucleotide comprising a nucleotide sequence, wherein the nucleotide sequence corresponds to an allele of SEQ ID NO:1, 2, 3 or 21.

Any of the foregoing isolated polynucleotides may be utilized in any recombinant DNA constructs (including suppression DNA constructs) of the present disclosure.

An isolated OSD1-3A polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:8; or (ii) a full complement of the nucleic acid sequence of (i), wherein the full complement and the nucleic acid sequence of (i) consist of the same number of nucleotides and are 100% complementary.

An isolated OSD1-3A polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:8.

An isolated OSD1-3A polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 5, 6, 7, or 22 and combinations thereof; or (ii) a full complement of the nucleic acid sequence of (i). Any of the foregoing isolated polynucleotides may be utilized in any recombinant DNA constructs (including suppression DNA constructs) of the present disclosure.

An isolated OSD1-3A polynucleotide comprising a nucleotide sequence, wherein the nucleotide sequence is hybridizable under stringent conditions with a DNA molecule comprising the full complement of SEQ ID NO:5, 6, 7, or 22. The isolated OSD1-3A protein of the present disclosure may also be a protein which is encoded by a nucleic acid comprising a nucleotide sequence hybridizable under stringent conditions with the complementary strand of the nucleotide sequence of SEQ ID NO:5, 6, or 7.

An isolated OSD1-3A polynucleotide comprising a nucleotide sequence, wherein the nucleotide sequence is derived from SEQ ID NO:5, 6, 7, or 22 by alteration of one or more nucleotides by at least one method selected from the group consisting of: deletion, substitution, addition and insertion.

An isolated OSD1-3A polynucleotide comprising a nucleotide sequence, wherein the nucleotide sequence corresponds to an allele of SEQ ID NO:5, 6, 7, or 22.

Nucleic acid molecules that are fragments of these nucleic acid sequences encoding Spo11, Rec8, OSD1-1A or OSD1-3A polypeptides are also encompassed by the embodiments. "Fragment" as used herein refers to a portion of the nucleic acid sequence encoding a Spo11, Rec8, OSD1-1A or OSD1-3A polypeptide. A fragment of a nucleic acid sequence may encode a biologically active portion of Spo11, Rec8, OSD1-1A or OSD1-3A polypeptide or it may be a fragment that can be used as a hybridization probe or PCR primer using methods disclosed below. Nucleic acid molecules that are fragments of a nucleic acid sequence encoding a Spo11, Rec8, OSD1-1A or OSD1-3A polypeptide comprise at least about 150, 180, 210, 240, 270, 300, 330, 360, 400, 450, 500, 550, 600, 650, 700, 750, 800, 850, 900, 950, 1000, 1050, 1100, 1150, 1200, 1250, 1300, 1350 or contiguous nucleotides or up to the number of nucleotides present in a full-length nucleic acid sequence encoding a Spo11, Rec8, OSD1-1A or OSD1-3A polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the Spo11, Rec8, OSD1-1A or OSD1-3A polypeptide and, hence, retain its respective Spo11, Rec8, OSD1-1A or OSD1-3A activity.

Any of the foregoing isolated polynucleotides may be utilized in any recombinant DNA constructs (including suppression DNA constructs) of the present disclosure. Accordingly, in certain embodiments, compositions (such as plants or seeds) comprising these isolated Spo11, Rec8, OSD1-1A, and/or OSD1-3A polynucleotides and polypeptides or combinations thereof are provided. Recombinant DNA constructs expressing the isolated Spo11, Rec8, OSD1-1A, and/or OSD1-3A polynucleotides or combinations thereof are also provided.

In certain embodiments, suppression Spo11, Rec8, OSD1-1A, and/or OSD1-3A polynucleotides or combinations thereof are disclosed. Also included herein are recombinant DNA constructs expressing the suppression Spo11, Rec8, OSD1-1A, and/or OSD1-3A polynucleotides or combinations thereof. Methods may include the use of any of these isolated or suppression Spo11, Rec8, OSD1-1A, and OSD1-3A polynucleotides, and the recombinant DNA constructs comprising them. Additionally, the present disclosure relates to a vector containing the recombinant DNA construct. Further, the vector containing the recombinant expression cassette or construct can facilitate the transcription and translation of the nucleic acid in a host cell. The present disclosure also relates to the host cells able to express the polynucleotides disclosed herein. A number of host cells could be used, such as but not limited to, microbial, mammalian, plant or insect.

Methods are provided to suppress the activity of an endogenous Spo11, Rec8, OSD1-1A, and/or OSD1-3A polynucleotide or polypeptide, or combinations thereof in a plant cell. In some aspects, suppressing activity also includes suppressing the expression level of the Spo11, Rec8, OSD1-1A, and OSD1-3A polynucleotide or polypeptide. Any suitable method or technique may be used. One of ordinary skill in the art would readily recognize a suitable control or reference to be utilized when assessing or measuring expression level or activity of Spo11, Rec8, OSD1-1A, and/or OSD1-3A polynucleotide or polypeptide in any embodiment of the present disclosure in which a control or reference is utilized (e.g., compositions or methods as described herein). For example, by way of non-limiting illustrations, a plant or plant cell comprising a modified Spo11, Rec8, OSD1-1A, and/or OSD1-3A polynucleotide or polypeptide; or Spo11, Rec8, OSD1-1A, and/or OSD1-3A suppression polynucleotide would be typically measured relative to a plant or plant cell not comprising the modified Spo11, Rec8, OSD1-1A, and/or OSD1-3A polynucleotide or polypeptide, or the Spo11, Rec8, OSD1-1A, and/or OSD1-3A suppression polynucleotide as the control or reference plant or plant cell. In some examples, the control is a wild type plant or cell. One skilled in the art will be able to determine Spo11, Rec8, OSD1-1A, and/or OSD1-3A expression level or activity using assays, such as PCR, Northern, and Western blot assays.

In certain embodiments, an endogenous gene of Spo11, Rec8, OSD1-1A, and/or OSD1-3A, or combinations thereof may be modified in a plant cell. Accordingly, the present disclosure is directed to a plant or plant cells comprising the modified Spo11, Rec8, OSD1-1A, and/or OSD1-3A. Another embodiment is the seed from the modified plant. In some embodiments, the modification gene is different than the gene in its native form in composition and/or genomic locus through deliberate human intervention. Methods and techniques to modify or alter Spo11, Rec8, OSD1-1A, and/or OSD1-3A genes, or combinations thereof are provided herein. In some examples, this includes altering the host plant native DNA sequence or a pre-existing recombinant sequence including regulatory elements, coding and/or non-coding sequences. In certain examples of genome editing approaches, endonucleases including but not limited to Cas endonuclease and guide RNA, are employed to delete, edit, insert or substitute all or part of a plant cell's endogenous Spo11, Rec8, OSD1-1A, and/or OSD1-3A genes or combinations thereof to suppress the respective endogenous Spo11, Rec8, OSD1-1A, and OSD1-3A activity. In some aspects, suppressing activity also includes suppressing the expression level of the Spo11, Rec8, OSD1-1A, and/or OSD1-3A polynucleotide or polypeptide.

In certain embodiments, the plant cell's endogenous Spo11, Rec8, or OSD1-1A, and/or OSD1-3A genes may be modified using genome editing technologies including but not limited to meganucleases, zinc finger nucleases, transcription activator-like effector nucleases (TALENS), CRISPR-Cas9 and RNA-guided endonucleases. Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex.

Endonucleases also include meganucleases, also known as homing endonucleases (HEases). Like restriction endonucleases, HEases bind and cut at a specific recognition site. However, the recognition sites for meganucleases are typically longer, about 18 bp or more. (See patent publication WO2012/129373 filed on Mar. 22, 2012). One step in the recombination process involves polynucleotide cleavage at or near the meganuclease recognition site. This cleaving activity can be used to produce a double-strand break. For reviews of site-specific recombinases and their recognition sites, see, Sauer (1994) Curr. Op. Biotechnol. 5:521-7; and Sadowski (1993) FASEB 7:760-7. In some examples the recombinase is from the Integrase or Resolvase families.

TAL effector nucleases are a class of sequence-specific nucleases that can be used to make double-strand breaks at specific target sequences in the genome of a plant or other organism. (Miller et al. (2011) *Nature Biotechnology* 29:143-148). Zinc finger nucleases (ZFNs) are engineered double-strand-break-inducing agents comprised of a zinc finger DNA binding domain and a double-strand-break-inducing agent domain. Recognition site specificity is conferred by the zinc finger domain, which typically comprises two, three, or four zinc fingers, for example having a C2H2 structure; however other zinc finger structures are known and have been engineered. Zinc finger domains are amenable for designing polypeptides which specifically bind a selected polynucleotide recognition sequence. Each zinc finger recognizes three consecutive base pairs in the target DNA. For example, a 3-finger domain recognizes a sequence of 9 contiguous nucleotides; with a dimerization requirement of the nuclease, two sets of zinc finger triplets are used to bind an 18-nucleotide recognition sequence.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax mediterranei, Streptococcus pyogenes, Anabaena,* and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

Cas gene relates to a gene that is generally coupled, associated or close to or in the vicinity of flanking CRISPR loci. The terms "Cas gene", "CRISPR-associated (Cas)

gene" are used interchangeably herein. A comprehensive review of the Cas protein family is presented in Haft et al. (2005) Computational Biology, PLoS Comput Biol 1(6): e60. doi:10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. Provisional Application No. 62/023,239, filed Jul. 11, 2014). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

The Cas endonuclease gene can be Cas9 endonuclease, or a functional fragment thereof, such as but not limited to, Cas9 genes listed in SEQ ID NOs: 462, 474, 489, 494, 499, 505, and 518 of WO2007/025097 published Mar. 1, 2007. The Cas endonuclease gene can be a plant, maize or soybean optimized Cas9 endonuclease, such as but not limited to a plant codon optimized *Streptococcus pyogenes* Cas9 gene that can recognize any genomic sequence of the form N(12-30)NGG. The Cas endonuclease can be introduced directly into a cell by any method known in the art, for example, but not limited to transient introduction methods, transfection and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. Provisional Application No. 62/023,239, filed Jul. 11, 2014). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In certain embodiments the nucleotide sequence to be modified can be a regulatory sequence such as a promoter, wherein the editing of the promoter comprises replacing the promoter (also referred to as a "promoter swap" or "promoter replacement") or promoter fragment with a different promoter (also referred to as replacement promoter) or promoter fragment (also referred to as replacement promoter fragment), wherein the promoter replacement results in any one of the following or any combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression in the same cell layer or other cell layer (such as but not limiting to extending the timing of gene expression in the tapetum of maize anthers; see e.g. U.S. Pat. No. 5,837,850 issued Nov. 17, 1998), a mutation of DNA binding elements and/or deletion or addition of DNA binding elements. The promoter (or promoter fragment) to be modified can be a promoter (or promoter fragment) that is endogenous, artificial, pre-existing, or transgenic to the cell that is being edited. The replacement promoter (or replacement promoter fragment) can be a promoter (or promoter fragment) that is endogenous, artificial, pre-existing, or transgenic to the cell that is being edited.

Promoter elements to be inserted can be, but are not limited to, promoter core elements (such as, but not limited to, a CAAT box, a CCAAT box, a Pribnow box, a and/or TATA box, translational regulation sequences and/or a repressor system for inducible expression (such as TET operator repressor/operator/inducer elements, or SulphonylUrea (Su) repressor/operator/inducer elements. The dehydration-responsive element (DRE) was first identified as a cis-acting promoter element in the promoter of the drought-responsive gene rd29A, which contains a 9 bp conserved core sequence, TACCGACAT (Yamaguchi-Shinozaki, K., and Shinozaki, K. (1994) *Plant Cell* 6, 251-264). Insertion of DRE into an endogenous promoter may confer a drought inducible expression of the downstream gene. Another example is ABA-responsive elements (ABREs) which contain a (C/T)ACGTGGC consensus sequence found to be present in numerous ABA and/or stress-regulated genes (Busk P. K., Pages M. (1998) Plant Mol. Biol. 37:425-435). Insertion of 35S enhancer or MMV enhancer into an endogenous promoter region will increase gene expression (U.S. Pat. No. 5,196,525). The promoter (or promoter element) to be inserted can be a promoter (or promoter element) that is endogenous, artificial, pre-existing, or transgenic to the cell that is being edited.

In certain embodiments, a suppression polynucleotide sequence is capable of suppressing the activity of the endogenous Spo11, Rec8, OSD1-1A, and/or OSD1-3A polypeptide(s) or combinations thereof disclosed elsewhere herein. In some aspects, suppressing activity includes suppressing the expression level of the Spo11, Rec8, OSD1-1A, and/or OSD1-3A polynucleotide or polypeptide. Suppression polynucleotides may be introduced into a plant cell to suppress endogenous gene(s) of Spo11, Rec8, OSD1-1A, and/or OSD1-3A, or combinations thereof using any suitable technique or method or mechanism that results in the suppression of Spo11, Rec8, OSD1-1A, and/or OSD1-3A activity. In certain embodiments, Spo11, Rec8, OSD1-1A, and/or OSD1-3A or combinations thereof are suppressed using anti-sense, cosuppression, viral-suppression, hairpin suppression, stem-loop suppression, RNAi-based approaches, and small RNA-based approaches. In certain examples, genome editing approaches, including but not limited to, Cas endonuclease and guide RNA, are employed to introduce into a plant cell's genome polynucleotides that suppress Spo11, Rec8, OSD1-1A, and/or OSD1-3A expression and/or activity. Examples of such Spo11, Rec8, OSD1-1A, and/or OSD1-3A suppression polynucleotides that may be used to suppress the expression of Spo11, Rec8, OSD1-1A, and/or OSD1-3A are provided herein elsewhere.

In some embodiments, Spo11, Rec8, OSD1-1A, and/or OSD1-3A suppression polynucleotides, or combinations thereof comprise polynucleotides for cosuppression. In certain embodiments for cosuppression, the polynucleotide is designed to express an RNA molecule corresponding to all or part of a messenger RNA encoding a Spo11, Rec8, OSD1-1A, and/or OSD1-3A polypeptide in the "sense" orientation.

Over expression of the RNA molecule can result in reduced expression of the native gene. In certain embodiments for cosuppression, the cosuppression polynucleotide linked to a heterologous promoter and expressed from a cosuppression expression cassette. Plant cells may be transformed with the cosuppression polynucleotide or cosuppression expression cassette and screened to identify those that show the greatest suppression of Spo11, Rec8, OSD1-1A, and/or OSD1-3A polypeptide expression.

The polynucleotide used for cosuppression may correspond to all or part of the sequence encoding the Spo11, Rec8, OSD1-1A, and/or OSD1-3A polypeptide, all or part of the 5' and/or 3' untranslated region of an Spo11, Rec8, OSD1-1A, and/or OSD1-3A polypeptide transcript or all or part of both the coding sequence and the untranslated regions of a transcript encoding an Spo11, Rec8, OSD1-1A, and/or OSD1-3A polypeptide. In some embodiments where the polynucleotide comprises all or part of the coding region for the Spo11, Rec8, OSD1-1A, and/or OSD1-3A polypeptide, the expression cassette is designed to eliminate the start codon of the polynucleotide so that no protein product will be translated.

Cosuppression may be used to suppress the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

In some embodiments, suppression of the expression of the Spo11, Rec8, OSD1-1A, and/or OSD1-3A polypeptide may be obtained by antisense suppression. For antisense suppression, the expression cassette is designed to express an RNA molecule complementary to all or part of a messenger RNA encoding the Spo11, Rec8, OSD1-1A, and/or OSD1-3A polypeptide. Over expression of the antisense RNA molecule can result in reduced expression of the native gene. Accordingly, multiple plant lines transformed with the antisense suppression expression cassette are screened to identify those that show the greatest inhibition of a Spo11, Rec8, OSD1-1A, and/or OSD1-3A polypeptide expression.

The polynucleotide for use in antisense suppression may correspond to all or part of the complement of the sequence encoding the Spo11, Rec8, OSD1-1A, and/or OSD1-3A polypeptide, all or part of the complement of the 5' and/or 3' untranslated region of the Spo11, Rec8, OSD1-1A, and/or OSD1-3A transcript or all or part of the complement of both the coding sequence and the untranslated regions of a transcript encoding the Spo11, Rec8, OSD1-1A, and/or OSD1-3A polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene, for example, Spo11, Rec8, OSD1-1A, and/or OSD1-3A. Generally, sequences of at least 50 nucleotides, 100 nucleotides, 200 nucleotides, 300, 400, 450, 500, 550, 600 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

In certain embodiments, the present disclosure includes suppression Spo11, Rec8, OSD1-1A and OSD1-3A polynucleotides for use in the methods described herein.

A Spo11 suppression polynucleotide may comprise all or part of: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:16, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with said all or part of a sense strand or antisense strand from which said region is derived, and wherein said target gene of interest encodes a Spo11 polypeptide; or (c) all or part of: (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 13, 14, 15, or 19, and combinations thereof, or (ii) a full complement of the nucleic acid sequence of (c)(i). In certain embodiments the Spo11 suppression polynucleotide is operably liked to at least one heterologous regulatory sequence (e.g., a promoter functional in a plant). For example, the Spo11 suppression polynucleotide may be inserted via gene editing or other approach into a plant chromosome and expressed so that it suppresses endogenous Spo11 expression or activity. The Spo11 suppression polynucleotide may be operably liked to at least one heterologous regulatory sequence (e.g., a promoter functional in a plant). In some instances, the Spo11 suppression polynucleotide may be operably liked to at least one heterologous regulatory sequence and expressed from a suppression DNA construct.

A Rec8 suppression polynucleotide may comprise all or part of: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:12, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with said all or part of a sense strand or antisense strand from which said region is derived, and wherein said target gene of interest encodes a Rec8 polypeptide; or (c) all or part of: (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 9, 10, 11 or 20, and combinations thereof, or (ii) a full complement of the nucleic acid sequence of (c)(i). In certain embodiments the Rec8 suppression polynucleotide is operably liked to at least one heterologous regulatory sequence (e.g., a promoter functional in a plant). For example, the Rec8 suppression polynucleotide may be inserted via gene editing or other approach into a plant chromosome and expressed so that it suppresses endogenous Rec8 expression or activity. The Rec8 suppression polynucleotide may be operably liked to at least one heterologous regulatory sequence (e.g., a promoter functional in a plant). In some instances, the Rec8 suppression polynucleotide may be operably liked to at least one heterologous regulatory sequence and expressed from a suppression DNA construct.

A OSD1-1A suppression polynucleotide may comprise all or part of: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:4, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with said all or part of a sense strand or antisense strand from which said region is derived, and wherein said target gene of interest encodes a OSD1-1A polypeptide; or (c) all or part of: (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 1, 2, 3 or 21, and combinations thereof, or (ii) a full complement of the nucleic acid sequence of (c)(i). In certain embodiments the OSD1-1A suppression polynucleotide is operably liked to at least one heterologous regulatory sequence (e.g., a promoter functional in a plant). For example, the OSD1-1A suppression polynucleotide may be inserted via gene editing or other approach into a plant chromosome and expressed so that it suppresses endogenous OSD1-1A expression or activity. The OSD1-1A suppression polynucleotide may be operably liked to at least one heterologous regulatory sequence (e.g., a promoter functional in a plant). In some instances, the OSD1-1A suppression polynucleotide may be operably liked to at least one heterologous regulatory sequence and expressed from a suppression DNA construct.

A OSD1-3A suppression polynucleotide may comprise all or part of: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO:8, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with said all or part of a sense strand or antisense strand from which said region is derived, and wherein said target gene of interest encodes a OSD1-3A polypeptide; or (c) all or part of: (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO:5, 6, 7 or 22, and combinations thereof, or (ii) a full complement of the nucleic acid sequence of (c)(i). In certain embodiments the OSD1-3A suppression polynucleotide is operably liked to at least one heterologous regulatory sequence (e.g., a promoter functional in a plant). For example, the OSD1-3A suppression polynucleotide may be inserted via gene editing or other approach into a plant chromosome and expressed so that it suppresses endogenous OSD1-3A expression or activity. The OSD1-3A suppression polynucleotide may be operably liked to at least one heterologous regulatory sequence (e.g., a promoter functional in a plant). In some instances, the OSD1-3A suppression polynucleotide may be operably liked to at least one heterologous regulatory sequence and expressed from a suppression DNA construct.

In some embodiments, suppression of the expression of a Spo11, Rec8, OSD1-1A, and/or OSD1-3A polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of a Spo11, Rec8, OSD1-1A, and/or OSD1-3A polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 1999/49029, WO 1999/53050, WO 1999/61631 and WO 2000/49035, each of which is herein incorporated by reference.

In some embodiments, inhibition of the expression of a Spo11, Rec8, OSD1-1A, and/or OSD1-3A polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295, and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene, for example, Spo11, Rec8, OSD1-1A, and/or OSD1-3A. Thus, it is the loop region that determines the specificity of the RNA interference. See, for example, WO 2002/00904, Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4):16499-16506; Sijen, et al., *Curr. Biol.* (2001) 11:436-440), herein incorporated by reference.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the Spo11, Rec8, OSD1-1A, and/or OSD1-3A polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

In some embodiments, the polynucleotide expressed by the expression cassette of the disclosure is catalytic RNA or has ribozyme activity specific for the messenger RNA of the Spo11, Rec8, OSD1-1A, and/or OSD1-3A polypeptide. Thus, the polynucleotide causes the degradation of the endogenous messenger RNA, resulting in reduced expression of the Spo11, Rec8, OSD1-1A, and/or OSD1-3A polypeptide. This method is described, for example, in U.S. Pat. No. 4,987,071, herein incorporated by reference.

RNA interference generally refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

In some embodiments, suppression of the expression of a Spo11, Rec8, OSD1-1A, and/or OSD1-3A polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425: 257-263, herein incorporated by reference.

In one embodiment, there is provided a method for the suppression of a target sequence comprising introducing into a cell a nucleic acid construct encoding a miRNA substantially complementary to the target. In certain embodiments, the target is the Spo11, Rec8, OSD1-1A, and/or OSD1-3A polynucleotides disclosed herein. In certain embodiments, maize OSD1-1A and OSD1-3A artificial microRNA (amiRNA) target sequences are those found in SEQ ID NO:17 and SEQ ID NO:18 respectively. In some embodiments the miRNA comprises about 19, 20, 21, 22, 23, 24 or 25 nucleotides. In some embodiments the miRNA comprises 21 nucleotides. In some embodiments the nucleic acid construct encodes the miRNA. In some embodiments the nucleic acid construct encodes a polynucleotide precursor which may form a double-stranded RNA, or hairpin structure comprising the miRNA.

In some embodiments, the nucleic acid construct comprises a modified endogenous plant miRNA precursor, wherein the precursor has been modified to replace the endogenous miRNA encoding region with a sequence designed to produce a miRNA directed to the target sequence. The plant miRNA precursor may be full-length of may comprise a fragment of the full-length precursor. In some embodiments, the endogenous plant miRNA precursor is from a dicot or a monocot. In some embodiments the endogenous miRNA precursor is from *Arabidopsis*, tomato, maize, soybean, sunflower, sorghum, canola, wheat, alfalfa, cotton, rice, barley, millet, sugar cane or switchgrass.

In some embodiments, the miRNA template, (i.e. the polynucleotide encoding the miRNA), and thereby the miRNA, may comprise some mismatches relative to the target sequence. In some embodiments the miRNA template has >1 nucleotide mismatch as compared to the target sequence, for example, the miRNA template can have 1, 2, 3, 4, 5, or more mismatches as compared to the target sequence. This degree of mismatch may also be described by determining the percent identity of the miRNA template to the complement of the target sequence. For example, the miRNA template may have a percent identity including about at least 70%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the complement of the target sequence. In certain embodiments, the target is the Spo11, Rec8, OSD1-1A, and/or OSD1-3A polynucleotides disclosed herein.

In some embodiments, the miRNA template, (i.e. the polynucleotide encoding the miRNA) and thereby the miRNA, may comprise some mismatches relative to the miRNA-star sequence. In some embodiments the miRNA template has >1 nucleotide mismatch as compared to the miRNA-star sequence, for example, the miRNA template can have 1, 2, 3, 4, 5, or more mismatches as compared to the miRNA-star sequence. This degree of mismatch may also be described by determining the percent identity of the miRNA template to the complement of the miRNA-star sequence. For example, the miRNA template may have a percent identity including about at least 70%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the complement of the miRNA-star sequence.

In certain embodiments, for miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of Spo11, Rec8, OSD1-1A, and/or OSD1-3A expression, the 22-nucleotide sequence is selected from a Spo11, Rec8, OSD1-1A, and/or OSD1-3A transcript sequence and contains 22 nucleotides of said Spo11, Rec8, OSD1-1A, and/or OSD1-3A sequence in sense orientation and 21 nucleotides of a corresponding antisense sequence that is complementary to the sense sequence. miRNA molecules are highly efficient at inhibiting the expression of endogenous genes and the RNA interference they induce is inherited by subsequent generations of plants.

In one embodiment, the polynucleotide encodes a zinc finger protein that binds to a gene encoding Spo11, Rec8, OSD1-1A, and/or OSD1-3A polypeptide, resulting in reduced expression of the cognate Spo11, Rec8, OSD1-1A, OSD1-3A gene. In particular embodiments, the zinc finger protein binds to a regulatory region of the Spo11, Rec8, OSD1-1A, and/or OSD1-3A gene. In other embodiments, the zinc finger protein binds to a messenger RNA encoding a Spo11, Rec8, OSD1-1A, and/or OSD1-3A polypeptide and prevents its translation. Methods of selecting sites for targeting by zinc finger proteins have been described, for example, in U.S. Pat. No. 6,453,242 and methods for using zinc finger proteins to inhibit the expression of genes in plants are described, for example, in US Patent Application Publication Number 2003/0037355, each of which is herein incorporated by reference.

In some embodiments, the polynucleotide encodes an antibody that binds to at least one Spo11, Rec8, OSD1-1A, and/or OSD1-3A polypeptide, or combinations thereof and suppresses the Spo11, Rec8, OSD1-1A, OSD1-3A activity of the respective Spo11, Rec8, OSD1-1A, OSD1-3A polypeptide. In another embodiment, the binding of the antibody results in increased turnover of the antibody-SPO11, REC8, OSD1-1A, and/or OSD1-3A complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

In some embodiments, the activity of a Spo11, Rec8, OSD1-1A, and/or OSD1-3A polypeptide is suppressed by disrupting the gene encoding the Spo11, Rec8, OSD1-1A, and/or OSD1-3A polypeptide, for example, using any method known in the art, including but not limited to genome editing approaches. In certain embodiments, the Spo11, Rec8, OSD1-1A, and/or OSD1-3A gene is disrupted by transposon tagging. In another embodiment, the Spo11, Rec8, OSD1-1A, and/or OSD1-3A gene is disrupted by mutagenizing plants using random or targeted mutagenesis, such as or TUSC mutations, and selecting for plants that have reduced Spo11, Rec8, OSD1-1A, and/or OSD1-3A activity, for example, expression level, or combinations thereof. Additional methods for suppressing the expression of an endogenous Spo11, Rec8, OSD1-1A, and/or OSD1-3A polypeptide in plants include ethyl methanesulfonate-induced mutagenesis and deletion mutagenesis. In addition, a fast and automatable method for screening for chemically induced mutations, TILLING (Targeting Induced Local Lesions In Genomes), using denaturing HPLC or selective endonuclease digestion of selected PCR products is also applicable may also be used. See, McCallum, et al., (2000) *Nat. Biotechnol.* 18:455-457, herein incorporated by reference.

As described elsewhere herein, the suppression polynucleotides can be introduced in a variety of ways. As discussed herein, one of skill will recognize the appropriate promoter to use to for use in driving expression of Spo11, Rec8, OSD1-1A, and/or OSD1-3A polynucleotides or suppression polynucleotides in a plant or plant cell. The suppression polynucleotides can be expressed in a specific manner, for example, using constitutive, inducible or tissue-preferred or developmentally regulated promoters that are discussed elsewhere herein. In one embodiment, the suppression polynucleotides is operably linked to a Spo11, Rec8, OSD1-1A or OSD1-3A promoter, variant or fragment thereof. The promoter may be the native promoter for the endogenous Spo11, Rec8, OSD1-1A or OSD1-3A gene, or heterologous to the endogenous Spo11, Rec8, OSD1-1A or OSD1-3A gene, for example, from another species or crop.

In certain embodiments, the suppression polynucleotides are expressed in a plant cell undergoing meiosis.

In certain embodiments, the disclosure includes a method for obtaining a maize plant with a modified endogenous Spo11 polynucleotide sequence. In certain aspects, the modified endogenous Spo11 disrupts the homologous pairing and subsequent recombination of chromosomes during meiosis in a plant cell. In certain aspects, the activity of the endogenous Spo11 polynucleotide or polypeptide is suppressed using genome editing approaches, for example, by genetically modifying the endogenous Spo11. In some approaches, the suppression results from a nucleotide modification of the endogenous maize Spo11 polynucleotide sequences. In some embodiments, the nucleotide modification is a deletion, addition, or substitution of one or more nucleotides. In certain embodiments, the suppression results from an amino modification of the endogenous Spo11 polypeptide sequence. In some embodiments, the amino acid modification is a deletion, addition, or substitution of one or more amino acids. In certain aspects, the activity of the endogenous Spo11 polynucleotide or polypeptide is suppressed using RNA-based silencing approaches, for example, antisense, microRNA, RNAi, or hairpin molecule, described elsewhere herein. In certain embodiments, the suppression of Spo11 is a knock-out of the gene.

In certain embodiments, the disclosure includes a method for obtaining a maize plant with a modified endogenous Rec8 polynucleotide sequence. In certain aspects, the modified endogenous Rec8 disrupts the orientation of kinetochores and subsequent random distribution of chromatids during meiosis II in a plant cell. In certain aspects, the activity of the endogenous Rec8 polynucleotide or polypeptide is suppressed using genome editing approaches, for example, by genetically modifying the endogenous Rec8. In some approaches, the suppression results from a nucleotide modification of the endogenous maize Rec8 polynucleotide sequences. In some embodiments, the nucleotide modification is a deletion, addition, or substitution of one or more nucleotides. In certain embodiments, the suppression results from an amino of modification of the endogenous Rec8 polypeptide sequence. In some embodiments, the amino acid modification is a deletion, addition, or substitution of one or more amino acids. In certain aspects, the activity of the endogenous Rec8 polynucleotide or polypeptide is suppressed using RNA-based silencing approaches, for example, antisense, microRNA, RNAi, or hairpin molecule, described elsewhere herein. In certain embodiments, the suppression of Rec8 is a knock-out of the gene.

In certain embodiments, the disclosure includes a method for obtaining a maize plant with a modified endogenous OSD1-1A polynucleotide sequence. In certain aspects, the modified endogenous OSD1-1A and modified endogenous OSD1-3A together disrupt the progression of meiosis II division in a plant cell and produce non-reduced gametes. In certain aspects, the activity of the endogenous OSD1-1A polynucleotide or polypeptide is suppressed using genome editing approaches, for example, by genetically modifying the endogenous OSD1-1A. In some approaches, the suppression results from a nucleotide modification of the endogenous maize OSD1-1A polynucleotide sequences. In some embodiments, the nucleotide modification is a deletion, addition, or substitution of one or more nucleotides. In certain embodiments, the suppression results from an amino modification of the endogenous OSD1-1A polypeptide sequence. In some embodiments, the amino acid modification is a deletion, addition, or substitution of one or more amino acids. In certain aspects, the activity of the endogenous OSD1-1A polynucleotide or polypeptide is suppressed using RNA-based silencing approaches, for example, antisense, microRNA, RNAi, or hairpin molecule, described elsewhere herein. In certain embodiments, the suppression of OSD1-1A is a knock-out of the gene.

In certain embodiments, the disclosure includes a method for obtaining a maize plant with a modified endogenous OSD1-3A polynucleotide sequence. In certain aspects, the modified endogenous OSD1-1A and modified endogenous OSD1-3A together disrupt the progression of meiosis II division in a plant cell and produce non-reduced gametes. In certain aspects, the activity of the endogenous OSD1-3A polynucleotide or polypeptide is suppressed using genome editing approaches, for example, by genetically modifying the endogenous OSD1-3A. In some approaches, the suppression results from a nucleotide modification of the endogenous maize OSD1-3A polynucleotide sequences. In some embodiments, the nucleotide modification is a deletion, addition, or substitution of one or more nucleotides. In certain embodiments, the suppression results from an amino modification of the endogenous OSD1-3A polypeptide sequences. In some embodiments, the amino acid modification is a deletion, addition, or substitution of one or more amino acids. In certain aspects, the activity of the endogenous OSD1-3A polynucleotide or polypeptide is suppressed using RNA-based silencing approaches, for example, antisense, microRNA, RNAi, or hairpin molecule, described elsewhere herein. In certain embodiments, the suppression of OSD1-3A is a knock-out of the gene. In certain embodiments, both OSD1-1A and OSD1-3A are suppressed in order to obtain disruption of the progression of meiosis II division in a maize cell.

In certain embodiments provided herein is a method of producing clonal, non-reduced, non-recombined maize seed by crossing a maize plant that comprises suppressed activity of an endogenous Spo11 polynucleotide or polypeptide, an endogenous Rec8 polynucleotide or polypeptide, an endogenous OSD1-1A polynucleotide or polypeptide, and an endogenous OSD1-3A polynucleotide or polypeptide with a male maize parent that enables the development of the clonal, non-reduced, non-recombined gamete into an embryo. A Tetraploid Haploid Inducer can be used to induce the clonal gamete to develop into an embryo and enable proper endosperm development (by maintaining the proper female:male genome ratio), which results in the production of clonal, non-reduced, non-recombined seed. As used herein, the term "Tetraploid Haploid Inducer" (THI) refers to a tetraploid version of a maize maternal haploid inducer line. A maize haploid inducer line is capable of inducing gynogenesis, resulting in the production of maternal haploid progeny that originate exclusively from the egg cell. As a tetraploid, THI can be used to induce maternal diploid progeny when used as a male in crosses with female lines capable of producing unreduced egg cells. Marker analysis of female meiotic behavior in unreduced eggs is greatly simplified by elimination of the male genome from the progeny. In certain aspects, the Tetraploid Haploid Inducer is the maize Tetraploid Haploid Inducer (w/R-navajo). The resulting seeds that are non-reduced, non-recombined, and may be grown into plants and the seed harvested from those plants.

In yet another embodiment, the present disclosure is directed to a transgenic plant or plant cells comprising the Spo11, Rec8, OSD1-1A, and/or OSD1-3A polynucleotides or suppression polynucleotides described herein or combinations thereof. The Spo11, Rec8, OSD1-1A, and/or OSD1-3A polynucleotides or suppression polynucleotides may be stably incorporated into the plant's genome or transiently expressed.

Preferred plants include but are not limited to maize, soybean, sunflower, sorghum, canola, wheat, alfalfa, cotton, rice, barley, tomato, switchgrass, *miscanthus*, triticale and millet. In another embodiment, the plant is a modified maize plant or maize plant cell. Another embodiment is the seed from the transgenic, modified plant. The plants of the disclosure can have altered Spo11, Rec8, OSD1-1A, OSD1-3A expression level or activity as compared to a control plant.

One embodiment of the current disclosure is a method of obtaining a maize plant that produces clonal, non-reduced, non-recombined gametes by suppressing in the maize plant the activity of an endogenous Spo11 polynucleotide or polypeptide, an endogenous Rec8 polynucleotide or polypeptide, an endogenous OSD1-1A polynucleotide or polypeptide, and an endogenous OSD1-3A polynucleotide or polypeptide. Accordingly, one embodiment is a maize plant that produces clonal, non-reduced, non-recombined gametes, where the maize plant comprises suppressed activity of an endogenous Spo11 polynucleotide or polypeptide, an endogenous Rec8 polynucleotide or polypeptide, an endogenous OSD1-1A polynucleotide or polypeptide, and an endogenous OSD1-3A polynucleotide or polypeptide. In some embodiments, the Spo11 polynucleotide is selected from the group consisting of: a polynucleotide that encodes the polypeptide of the sequence set forth in SEQ ID NO:16; a polynucleotide comprising the sequence set forth in SEQ ID NO:13, 14, 15, or 19; and a polynucleotide having at least 80% sequence identity to the sequence set forth in SEQ ID NO: 13, 14, 15, or 19 and the Spo11 polypeptide is selected from the group consisting of: a polypeptide comprising the sequence set forth in SEQ ID NO: 16; a polypeptide that is at least 80% identical to the amino acid sequence of SEQ ID NO:16; a polypeptide that is encoded by a nucleic acid molecule comprising a nucleotide sequence that is at least 80% identical to the sequence set forth in SEQ ID NO:13, 14 or 15. In some embodiments, the Rec8 polynucleotide is selected from the group consisting of: a polynucleotide that encodes the polypeptide of the sequence set forth in SEQ ID NO:12, a polynucleotide comprising the sequence set forth in SEQ ID NO:9, 10, 11 or 20; and a polynucleotide having at least 80% sequence identity to the sequence set forth in SEQ ID NO: 9, 10, 11 or 20; and the Rec8 polypeptide is selected from the group consisting of: a polypeptide comprising the sequence set forth in SEQ ID NO: 12; a polypeptide that is at least 80% identical to the amino acid sequence of SEQ ID NO:12; a polypeptide that is encoded by a nucleic acid molecule comprising a nucleotide sequence that is at least 80% identical to the sequence set forth in SEQ ID NO:9, 10 or 11. In some embodiments, the endogenous OSD1-1A polynucleotide or polypeptide is selected from the group consisting of: a polynucleotide that encodes the polypeptide of the sequence set forth in SEQ ID NO:4; a polynucleotide comprising the sequence set forth in SEQ ID NO:1, 2, 3 or 21; and a polynucleotide having at least 80% sequence identity to the sequence set forth in SEQ ID NO: 1, 2, 3, or 21; and the OSD1-1A polypeptide is selected from the group consisting of: a polypeptide comprising the sequence set forth in SEQ ID NO:4; a polypeptide that is at least 80% identical to the amino acid sequence set forth in SEQ ID NO:4; a polypeptide that is encoded by a nucleic acid molecule comprising a nucleotide sequence that is at least 80% identical to the sequence set forth in SEQ ID NO:1, 2 or 3. In some embodiments, the endogenous OSD1-3A polynucleotide is selected from the group consisting of: a polynucleotide that encodes the polypeptide of the sequence set forth in SEQ ID NO:8 a polynucleotide comprising the sequence set forth in SEQ ID NO:5, 6, 7, or 22; and a polynucleotide having at least 80% sequence identity to the sequence set forth in SEQ ID NO:5, 6, 7, or 22 and the OSD1-3A polypeptide is selected from the group consisting of: a polypeptide comprising the sequence set forth in SEQ ID NO:8; a polypeptide that is at least 80% identical to the amino acid sequence of SEQ ID NO:8; a polypeptide that is encoded by a nucleic acid molecule comprising a nucleotide sequence that is at least 80% identical to the sequence set forth in SEQ ID NO: 5, 6 or 7.

In certain embodiments, the activity of the endogenous Spo11 polynucleotide or polypeptide, Rec8 polynucleotide or polypeptide, OSD1-1A polynucleotide or polypeptide, and/or OSD1-3A polynucleotide or polypeptide, or combinations thereof is suppressed using genome editing. In certain embodiments, the suppression of the Spo11, Rec8, OSD1-1A or OSD1-3A gene is a knock-out of the gene. In some approaches, the suppression results from a nucleotide modification of the endogenous Spo11, Rec8, OSD1-1A or OSD1-3A polynucleotide sequences. In some embodiments, the nucleotide modification is a deletion, addition, or substitution of one or more nucleotides. In certain embodiments, the suppression results from an amino modification of the endogenous Spo11, Rec8, OSD1-1A or OSD1-3A polypeptide sequence. In some embodiments, the amino acid modification is a deletion, addition, or substitution of one or more amino acids. In certain embodiments, the activity of the endogenous Spo11, Rec8, OSD1-1A or OSD1-3A polynucleotide or polypeptide is suppressed using RNA-based silencing approaches, for example, antisense, microRNA, RNAi, or hairpin molecule, described elsewhere herein.

In certain embodiments, the gene editing approach and anti-sense, cosuppression, viral-suppression, hairpin suppression, stem-loop suppression, RNAi-based approaches, and small RNA-based approaches are used alternatively or in addition to suppress activity of the endogenous Spo11, Rec8, OSD1-1A or OSD1-3A polynucleotide or polypeptides, thereby producing non-reduced, non-recombined and/or clonal gametes or combinations thereof. As one example, the suppression of both OSD1-1A and OSD1-3A in maize results in the disruption of meiosis and non-reduction of gametes. In another example, the suppression of both Spo11 and Rec8 in maize results in non-recombined gametes. With suppression of all four (Spo11, Rec8, OSD1-1A and OSD1-3A) in maize, non-reduced, non-recombined, clonal gametes may be produced. In some examples, the suppressed Spo11, Rec8, OSD1-1A or OSD1-3A polynucleotides or polypeptides are in a maize plant or plant cell.

In certain embodiments, the methods and compositions include a plant cell that has the modified endogenous Spo11, Rec8, OSD1-1A and/or OSD1-3A gene and/or suppression polynucleotide targeting Spo11, Rec8, OSD1-1A and/or OSD1-3A or combinations thereof. The plant may produce non-reduced, non-recombined and/or clonal female and/or male gametes. In other embodiments, the plant cell having the modified endogenous Spo11, Rec8, OSD1-1A and/or OSD1-3A gene or suppression polynucleotides targeting Spo11, Rec8, OSD1-1A and/or OSD1-3A or combinations thereof may be combined with one or more genes involved in recombination that have been modified, for example, by gene-editing technologies, to have decreased recombination activity in order to create plants that produce non-reduced, or non-reduced and non-recombined, female and/or male gametes. Additionally, the modified Spo11, Rec8, OSD1-1A and/or OSD1-3A gene and/or Spo11, Rec8, OSD1-1A and/or OSD1-3A suppression polynucleotides can be combined with other genes that are modified and/or other suppression polynucleotides that target other genes of interest. For example, the plant cell having the modified endogenous Spo11, Rec8, OSD1-1A or OSD1-3A gene or suppression polynucleotides targeting Spo11, Rec8, OSD1-1A or OSD1-3A may be combined or stacked with a suppression polynucleotide that targets genes that play a role in recombination in order to create plants that produce male and/or female gametes that are clonal, non-reduced and non-recombined or combinations thereof. For example, the recombination target genes include but are not limited to PRD1 (De Must et al, (2007) EMBO J. 26:4126-4137), TAM, TDM, Ago 104 (Singh et al, (2011) Plant Cell. 23:443-458), AMI, AM2, PAM1, PAM2, AS1, DSY1, DY1, ST1, ELI, DV1, VA1, VA2, POI, NRF4, and the like and combinations thereof.

Plant cells from the non-reduced, non-recombined and/or clonal female or male gametes can be stacked with traits desirable for disease or herbicide resistance (e.g., fumonisin detoxification genes (U.S. Pat. No. 5,792,931); avirulence and disease resistance genes (Jones et al, (1994) Science 266:789-793; Martin et al, (1993) Science 262: 1432-1436; Mindrinos et al, (1994) Cell 78: 1089-1099); acetolactate synthase (ALS) mutants that lead to herbicide resistance, such as the S4 and/or Hra mutations; inhibitors of glutamine synthase, such as phosphinothricin or basta (e.g., bar gene); and glyphosate resistance (EPSPS gene); traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al, (1988) J. Bacteriol. 170:5837-5847) facilitate expression of polyhydroxyalkanoates (PHAs)), the disclosures of which are herein incorporated by reference. One could also combine various polynucleotides, for example, polynucleotides providing agronomic traits such as male sterility (e.g., see U.S. Pat. No. 5,583,210), stalk strength, flowering time, or transformation technology traits, such as cell cycle regulation or gene targeting (e.g., WO 99/61619, WO 00/17364, and WO 99/25821), the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

In certain embodiments, methods are provided herein for producing clonal, non-recombined, and non-reduced male and/or female gametes or combinations thereof as well as and methods of maintaining clonality in offspring. Clonality may be determined using any suitable technique, for example, comparing the SNP pattern of the hybrid progenitor plants with progeny plants using heterozygous SNP markers. In some embodiments, the method comprises introducing into a plant a modification, for example, a suppression polynucleotide that suppresses the activity of the endogenous Spo11, Rec8, OSD1-1A and OSD1-3A polynucleotides or polypeptides, or combinations thereof, thereby producing clonal, non-reduced, and/or non-reduced male or female gametes or combinations thereof. In certain embodiments, the method comprises modifying an endogenous Spo11, Rec8, OSD1-1A and/or OSD1-3A target polynucleotides, for example, Spo11, Rec8, OSD1-1A and/or OSD1-3A genes, using gene editing approaches.

A further embodiment includes methods of maintaining clonality in a progeny plant that includes regenerating a progeny plant from a parent plant that has non-reduced, non-recombined clonal female or male gametes and has the same genotype as the parent plant. In some examples, the endogenous Spo11, Rec8, OSD1-1A and OSD1-3A gene is suppressed in the parent and progeny plant. In an aspect, the methods disclosed herein can further comprise the step of introducing into the plant genome a suppression of the endogenous Spo11, Rec8, OSD1-1A and OSD1-3A gene or combinations thereof, and regenerating a plant having such an altered genome.

In certain embodiments, the maize plant is a hybrid. In certain embodiments, the maize plant is an inbred. In certain embodiments, the maize plant is a female or male parent. Gametes obtained from this plant may be clonal, non-reduced, non-recombined gametes. The gametes may be male or female gametes or combinations thereof.

One embodiment of the disclosure includes a method of obtaining a maize plant that produces clonal, non-reduced, non-recombined male and/or female gametes. In certain embodiments, maize plants that have suppressed activity with respect to its endogenous Spo11, Rec8, OSD1-1A, and OSD1-3A polynucleotides and polypeptides are either heterozygous or homozygous for the suppression. These plants may be crossed, intercrossed, or selfed until a maize plant is obtained that comprises suppressed activity for each of these endogenous genes: Spo11, Rec8, OSD1-1A and OSD1-3A activity. In certain embodiments, Spo11 and Rec8 heterozygotes are intercrossed to generate homozygous knockouts of Spo11 and Rec8 since homozygote knock-outs of Spo11 and Rec8 in maize are individually male and female sterile and cannot be intercrossed.

In some embodiments, the homozygous suppression is caused by knocking out the gene. In certain embodiments, the maize plant is a hybrid. In certain embodiments, the maize plant is an inbred. In certain embodiments, the maize plant is a female or male parent. Gametes obtained from this plant may be clonal, non-reduced, non-recombined male and/or female gametes. Using methods described herein, seed produced from this plant may produce progeny that are non-reduced, non-recombined and clonal with respect to the parent plant, for example, when combined with haploid induction, parthenogenic or genome elimination approaches.

In certain embodiments, a method of producing a plant that comprises clonal, non-reduced and non-recombined female or male gametes or combinations thereof as compared with the parent plant comprises intercrossing or selfing a maize plant that has suppressed activity with respect to its endogenous Spo11, Rec8, OSD1-1A, and OSD1-3A polynucleotides and polypeptides. The resulting maize plant may be heterozygous, homozygous or a combination thereof for suppression of Spo11, Rec8, OSD1-1A, and OSD1-3A activity. For example, a maize plant is obtained from this method may be homozygous for the suppressed endogenous Spo11, Rec8, OSD1-1A and OSD1-3A activity. In certain embodiments, the suppression may be heterozygous, homozygous or a combination thereof. In some embodiments, the homozygous suppression is caused by knocking out the gene. In certain embodiments, the maize plant is a hybrid. In certain embodiments, the maize plant is an inbred. In certain embodiments, the maize plant is a female or male parent. Gametes obtained from this plant may be clonal, non-reduced, non-recombined male or female gametes.

The female parent that has suppressed Spo11, Rec8, and OSD1-1A, and OSD1-3A activity may be crossed with a tetraploid haploid inducer (THI) serving as a male parent to produce seed that is non-reduced and non-recombined. With respect to maize, the non-reduced and non-recombined seed may be diploid "haploids" (2n chromosome number) following pollination with the THI and have chromosomes only from the female parent. This will allow for clonal reproduction of the parent plant through seeds.

To facilitate with the identification of non-reduced and non-recombined seed, in certain embodiments, the tetraploid haploid inducer (THI) male parent comprises w/R-nj. See, WO2016179522 published application, herein incorporated by reference in its entirety. The use of w/R-nj in this method allows for the visual selection of non-reduced and non-recombined progeny since the haploid kernels with the female parent chromosomes will have a dark endosperm and normal (light-colored) embryo relative to regular seed produced from male and female parents which will have both dark endosperm and dark embryo. In this manner, 2n "haploids" may be identified by selecting seed with a colored endosperm cap and a colorless embryo. The other seeds (non-haploid seeds) may be tetraploids produced following pollination with a THI.

The seeds may be further evaluated, for example, by growing a plant from the non-reduced and non-recombined seed to determine whether the plant resembles and has the phenotype of the female parent plant, for example, when the plant is maize, whether the plant has similarities in plant height, maturity, flag leaf, and/or tassel phenotype. Alternatively or in addition, the heterozygous SNP pattern can be determined and compared to the SNP pattern of the hybrid progenitor plants. The SNP pattern from the parent and from the non-reduced and non-recombined progeny plants should share the same SNP pattern, indicating that no recombination had occurred in the progeny plants. The plants may be evaluated for ploidy status, for example, diploid, haploid or tetraploid status, to determine whether a reduction division in meiosis occurred. In certain instances, progeny plants can exhibit male sterility and/or reduced female fertility.

In certain embodiments, a parent plant homozygous for Spo11, Rec8, OSD1-1A, and OSD1-3A suppression comprises a haploid inducer gene so that non-recombined, non-reduced clonal progeny plants may be self-generated. Examples of haploid inducer genes include but are not limited to Matrilineal (MTL) gene. See, for example, Nature. 542:105-109 (2017), herein incorporated by reference in its entirety.

In certain embodiments, methods are provided for producing a plant that produces clonal, non-reduced, non-recombined seeds. For example, the female gametophyte or gamete produced using the methods and compositions described herein may undergo genome elimination to produce clonal, non-reduced, non-recombined maize seed using any suitable genome elimination approach. In certain embodiments, the method includes crossing a maize plant suppressed for the activity of an endogenous Spo11 polynucleotide or polypeptide, an endogenous Rec8 polynucleotide or polypeptide, an endogenous OSD1-1A polynucleotide or polypeptide, and an endogenous OSD1-3A polynucleotide or polypeptide with a maize male plant expressing a modified CENH3. Plants with modified CENH3 genes and polypeptides are described in U.S. Pat. Nos. 9,215,849 and 8,618,354, herein incorporated by reference in their entirety. In certain embodiments, the modified CENH3 allows for the elimination of the male or female parent genome in the zygote resulting from the cross of these two plants, such that the resulting progeny is non-recombined, non-reduced and clonal of one of the parent plants. In this manner, the seed obtained from a plant produced from this method allow for the clonal reproduction of the maize plant through seed.

In certain embodiments, methods are provided for producing a plant that produces clonal, non-reduced, non-recombined seeds, where the seeds comprises parthenogenetically-derived clonal embryos. For example, the female gametophyte or gamete produced using the methods and compositions described herein may undergo parthenogenesis to produce clonal, non-reduced, non-recombined maize seed using any suitable parthenogenic approach. In certain embodiments, the method includes crossing a maize plant suppressed for the activity of an endogenous Spo11 polynucleotide or polypeptide, an endogenous Rec8 polynucleotide or polypeptide, an endogenous OSD1-1A polynucleotide or polypeptide, and an endogenous OSD1-3A polynucleotide or polypeptide with a maize male plant expressing with a male parent that comprises a gene that induces a gamete to divide as an embryo. Exemplary genes that induce a gamete to divide as an embryo include but are not limited to BBML genes. See, for example, the ASGR-BBML gene in US Patent Application Publication No. 20160304901, incorporated herein by reference in its entirety. The resulting seeds obtained from this cross are clonal, non-reduced, non-recombined seeds. Plants produced from this method allow for the clonal reproduction of the maize plant through seed. In the methods described herein, the parent plant may be a hybrid plant.

Various types of promoters can be employed in the methods and compositions provided herein. Promoters can drive expression in a manner that is cell-type-preferred, cell-type-specific, tissue-preferred or tissue-specific. Examples of promoters under developmental control include promoters that preferentially initiate transcription in certain tissues, such as leaves, roots, seeds or ovules. Such promoters are referred to as "tissue preferred". Promoters which initiate transcription only in certain tissue are referred to as "tissue specific". A "cell type" preferred promoter primarily drives expression in certain cell types in one or more organs, for example, vascular cells in roots, leaves or ovules. An "inducible" or "repressible" promoter is a promoter which is under environmental or chemical control. Examples of environmental conditions that may affect transcription by inducible promoters include anaerobic conditions or the presence of light. Tissue specific, tissue preferred, cell type specific, cell type preferred and inducible promoters constitute the class of "non-constitutive" promoters. A "constitutive" promoter is a promoter that is active under most environmental conditions and in all tissues throughout development.

Non-limiting examples of constitutive promoters include, for example, the core promoter of the Rsyn7 promoter and other constitutive promoters disclosed in WO 1999/43838 and U.S. Pat. No. 6,072,050; the core CaMV 35S promoter (Odell et al, (1985) Nature 313:810-812); the rice actin promoter (McElroy et al., (1990) Plant Cell 2: 163-171); the ubiquitin promoter (Christensen et al, (1989) Plant Mol. Biol. 12:619-632 and Christensen et al, (1992) Plant Mol. Biol. 18:675-689); the pEMU promoter (Last et al, (1991) Theor. Appl. Genet. 81:581-588); the MAS promoter (Velten et al, (1984) EMBO J. 3:2723-2730); the ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142 and 6,177,611.

One of skill will recognize that the sequences encoding elements or polypeptides can be placed into an expression cassette or constructs. Expression cassettes or constructs are discussed elsewhere herein. Any promoter of interest can be operably linked to the sequence encoding the elements or polypeptides, including, for example, constitutive promoters, tissue-preferred promoters, tissue-specific promoters, including promoters that are functional during meiosis. Such promoters have been described elsewhere herein or are known in the art.

By "promoter" is intended a regulatory region of DNA usually comprising a TATA box capable of directing RNA polymerase II to initiate RNA synthesis at the appropriate transcription initiation site for a particular polynucleotide sequence. A promoter may additionally comprise other recognition sequences generally positioned upstream or 5' to the TATA box, referred to as upstream promoter elements, which influence the transcription initiation rate. The promoter sequences disclosed herein regulate (i.e., activate) transcription from the promoter region.

In some embodiments, the methods and compositions include isolated polynucleotides comprising Spo11, Rec8, OSD1-1A, and/or OSD1-3A upstream region sequences. The Spo11, Rec8, OSD1-1A, and/or OSD1-3A upstream region nucleotide sequences include those set forth in SEQ ID NOS:19, 20, 21 and 22, active variants and fragments thereof. In one embodiment, an expression construct includes any of the polynucleotides set forth in SEQ ID NOS: 19, 20, 21 and 22 operably linked to the polynucleotide of interest or any polynucleotide having at least 95%, 96%, 97%, 98% or 99% sequence identity to the sequence set forth in SEQ ID NO:19, 20, 21 and 22, wherein said polynucleotide retains the ability to direct expression of an operably linked polynucleotide in prior to or during meiosis.

Fragments and variants of each of the upstream region nucleotide sequences set forth in SEQ ID NOS:19, 20, 21 and 22 are further provided herein. Fragments of a upstream region polynucleotide may retain biological activity and, hence, retain transcriptional regulatory activity. Thus, fragments of a upstream region nucleotide sequence may range from at least about 20 nucleotides, about 50 nucleotides, about 100 nucleotides, and up to the full-length polynucleotide of the disclosure. Polynucleotides that are fragments of the upstream region polynucleotides comprise at least 16, 20, 50, 75, 100, 150, 200, 250, 300, 350, 400, 450, 500, 550, or 600, nucleotides.

For an upstream region polynucleotide, a variant comprises a deletion and/or addition of one or more nucleotides at one or more internal sites within the native polynucleotide and/or a substitution of one or more nucleotides at one or more sites in the native polynucleotide. Generally, variants of a particular upstream region polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Thus, any of the Spo11, Rec8, OSD1-1A, and/or OSD1-3A upstream region sequences, variants, and fragments thereof may be utilized to regulate a number of genes and developmental processes prior to or during meiosis. The Spo11, Rec8, OSD1-1A, and/or OSD1-3A promoter may be used to ectopically express an RNA resulting in protein production, silencing, gene modification, modification of other RNA(s), or catalysis of a reaction.

As discussed herein, various promoters can be employed in the methods and compositions provided herein, including: promoters to express sequences encoding suppression polynucleotides that suppress Spo11, Rec8, OSD1-1A, and/or OSD1-3A activity, for example, maize ubiquitin promoter, soy ubiquitin promoter, any of the upstream region sequences described herein. A Spo11, Rec8, OSD1-1A, and/or OSD1-3A upstream region sequence, variant, or fragment thereof can be operably linked to any of the sequences encoding suppression polynucleotides or polypeptides disclosed herein or known in the art. In one embodiment, the Spo11, Rec8, OSD1-1A, and/or OSD1-3A upstream region may be utilized in constructs designed to modify or alter the meiotic process. In such an embodiment, the construct may be used to express suppression polynucleotides that target LAM, OSD1, SPOII, TDM, PRD1, PRD2, PRD3, DFOI, REC8, AMI, AM2, PAM1, PAM2, AS1, DSY1, DY1, ST1, ELI, DV1, VA1, VA2 and/or POL.

It is recognized that additional domains can be added to the upstream region sequences disclosed herein and thereby modulate the level of expression, the developmental timing of expression, or the tissue type that expression occurs in. See, particularly, Australian Patent Number AU-A-77751/94 and U.S. Pat. Nos. 5,466,785 and 5,635,618.

Any of the promoter sequences employed herein can be modified to provide for a range of expression levels of the heterologous nucleotide sequence. Thus, less than the entire promoter region may be utilized and the ability to drive expression of the nucleotide sequence of interest retained. It is recognized that expression levels of the mRNA may be altered in different ways with deletions of portions of the promoter sequences. The mRNA expression levels may be decreased, or alternatively, expression may be increased as a result of promoter deletions if, for example, there is a negative regulatory element (for a repressor) that is removed during the truncation process. Generally, at least about 20 nucleotides of an isolated promoter sequence will be used to drive expression of a nucleotide sequence.

Methods are available in the art for determining if a promoter sequence retains the ability to regulate transcription in the desired temporal and spatial pattern. Such activity can be measured by Northern blot analysis. See, for example, Sambrook et al, (1989) Molecular Cloning: A Laboratory Manual (2d ed., Cold Spring Harbor Laboratory Press, Plainview, N.Y.), herein incorporated by reference. Alternatively, biological activity of the promoter can be measured using assays specifically designed for measuring the activity and/or level of the polypeptide being expressed from the promoter. Such assays are known in the art.

It is recognized that to increase transcription levels, enhancers may be utilized in combination with the promoter disclosed herein. Enhancers are nucleotide sequences that act to increase the expression of a promoter region. Enhancers are known in the art and include the SV40 enhancer region, the 35 S enhancer element, and the like. Some enhancers are also known to alter normal promoter expression patterns, for example, by causing a promoter to be expressed constitutively when without the enhancer, the same promoter is expressed only in one specific tissue or a few specific tissues.

Modifications of the promoters or upstream region sequences disclosed herein can provide for a range of expression of the heterologous nucleotide sequence. Thus, they may be modified to be weak promoters or strong promoters. Generally, a "weak promoter" means a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level or at about 1/10 transcripts to about 1/100 transcripts to about 1/1,000 transcripts.

The polynucleotides comprising the Spo11, Rec8, OSD1-1A, and/or OSD1-3A upstream region sequences disclosed herein, see, for example, SEQ ID NOS:19, 20, 21, or 22, as well as variants and fragments thereof, are useful in the genetic manipulation of any host cell, preferably plant cell.

The Spo11, Rec8, OSD1-1A, and/or OSD1-3A upstream region sequences disclosed herein, see, for example, SEQ ID NOS: 19, 20, 21, or 22, as well as variants and fragments thereof may be operably linked to a heterologous polynucleotide of interest. In this manner, the Spo11, Rec8, OSD1-1A, and/or OSD1-3A promoter polynucleotides of the disclosure are provided in expression cassettes along with a polynucleotide sequence of interest for expression in the host cell of interest. The Spo11, Rec8, OSD1-1A, and/or OSD1-3A promoter sequences of the disclosure may be useful in regulating the temporal and/or the spatial expression of polynucleotides of interest during meiosis.

As disclosed elsewhere herein, the Spo11, Rec8, OSD1-1A, and/or OSD1-3A upstream region sequences may be targets for Spo11, Rec8, OSD1-1A, and/or OSD1-3A suppression polynucleotides, including but not limited to promoter-inverted repeats or hairpinRNA.

Methods are also provided for the use of the Spo11, Rec8, OSD1-1A, and OSD1-3A polynucleotide and polypeptide sequences disclosed herein to affect meiosis. In certain embodiments, the method comprises increasing the activity or level of the Spo11, Rec8, OSD1-1A, and OSD1-3A polynucleotide and polypeptide sequences in a plant or plant part.

Numerous methods for introducing foreign genes into plants are known and can be used to insert a Spo11, Rec8, OSD1-1A, and/or OSD1-3A polynucleotide into a plant host, including biological and physical plant transformation protocols. See, e.g., Miki, et al., "Procedure for Introducing Foreign DNA into Plants," in METHODS IN PLANT MOLECULAR BIOLOGY AND BIOTECHNOLOGY, Glick and Thompson, eds., CRC Press, Inc., Boca Raton, pp. 67-88 (1993). The introduction of DNA constructs, for example, recombinant or suppression DNA constructs, of the present disclosure into plants may be carried out by any suitable technique, including but not limited to direct DNA uptake, chemical treatment, electroporation, microinjection, cell fusion, infection, vector-mediated DNA transfer, bombardment, or Agrobacterium-mediated transformation. Techniques for plant transformation and regeneration have been described in International Patent Publication WO 2009/006276, the contents of which are herein incorporated by reference.

Expression cassettes and vectors and in vitro culture methods for plant cell or tissue transformation and regeneration of plants are known and available. See, e.g., Gruber, et al., "Vectors for Plant Transformation," in METHODS IN PLANT MOLECULAR BIOLOGY AND BIOTECHNOLOGY, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) Biotechniques 4:320-334 and U.S. Pat. No. 6,300,543), electroporation (Riggs, et al., (1986) Proc. Natl. Acad. Sci. USA 83:5602-5606, direct gene transfer (Paszkowski, et al., (1984) EMBO J. 3:2717-2722) and ballistic particle acceleration (see, for example, Sanford, et al., U.S. Pat. No. 4,945,050; WO 1991/10725 and McCabe, et al., (1988) Biotechnology 6:923-926). Also see, Tomes, et al., Direct DNA Transfer into Intact Plant Cells Via Microprojectile Bombardment. pp. 197-213 in Plant Cell, Tissue and Organ Culture, Fundamental Methods. eds. Gamborg and Phillips. Springer-Verlag Berlin Heidelberg New York, 1995; U.S. Pat. No. 5,736,369 (meristem) 185), all of which are herein incorporated by reference. Descriptions of the Agrobacterium vector systems and methods for Agrobacterium-mediated gene transfer are provided in Gruber, et al., supra; Miki, et al., supra and Moloney, et al., (1989) Plant Cell Reports 8:238.

Once transformed, these cells can be used to regenerate transgenic plants. Examples of such methods for regenerating plant tissue are disclosed in Shahin, (1985) Theor. Appl. Genet. 69:235-40; U.S. Pat. No. 4,658,082; Simpson, et al., supra and U.S. patent application Ser. Nos. 913,913 and 913,914, Both Filed Oct. 1, 1986, as referenced in U.S. Pat. No. 5,262,306, issued Nov. 16, 1993, the entire disclosures therein incorporated herein by reference.

EXAMPLES

The present disclosure is further illustrated in the following Examples, in which parts and percentages are by weight and degrees are Celsius, unless otherwise stated. It should be understood that these Examples, while indicating embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims. This disclosure can be better understood by reference to the following non-limiting examples. It will be appreciated by those skilled in the art that other embodiments of the disclosure may be practiced without departing from the spirit and the scope of the disclosure as herein disclosed and claimed.

Example 1: Plant Materials of Mime (Mitosis Instead of Meiosis) Parent Plants

MiMe parent plants were a mixture of Zmspo11/Zmrec8 double homozygous TUSC insertion mutants (Golubovskaya I, Hamant O, Timofejeva L, Wang C R, Braun D, Meeley R, Cande W Z (2006) Alleles of afd1 dissect REC8 functions during meiotic prophase I. Journal of Cell Science 119: 3306-3315) and a transgenic line containing two artificial miRNA's (amiRNA) targeting ZmOSD1-1A and ZmOSD1-3A. Incompletely penetrant transgenic amiRNA lines silencing ZMOSD1-1A and ZmOSD1-3A that gave both reduced and non-reduced male and female gametes were selected for crossing with Zmspo11/Zmrec8 double heterozygous plants. These plants were self-pollinated, and progeny were analyzed with gene specific markers to determine zygosity of Zmspo11, Zmrec8 and ZMOSD1-1A/ZMOSD1-3A amiRNAs. Plants homozygous for Zmspo11 and Zmrec8 and hemi- or homo-zygous for ZMOSD1A-1/ZMOSD1-3A amiRNAs were selected (frequency 1/32-1/64).

TABLE 2

SNP marker analysis of progeny from three hybrid MiMe female parents

| MiMe Hybrid Parent Plant | Progeny | SNP marker analysis |
|---|---|---|
| Hybrid female #1 | 2 - 2n "haploid" progeny | 119 heterozygous SNP markers tested across all 10 chromosomes. Each with same SNP marker profile as Hybrid Female #1 |
| Hybrid female #2 | 4 - 2n "haploid" progeny | 114 heterozygous SNP markers tested across all 10 chromosomes. Each with same SNP marker profile as Hybrid Female #2 |
| Hybrid female #3 | 4 - 2n "haploid" progeny | 128 heterozygous SNP markers tested across all 10 chromosomes. Each with same SNP marker profile as Hybrid Female #3. |

What is claimed is:

1. A maize plant that produces clonal, non-reduced, non-recombined gametes, wherein the maize plant comprises:
   a) eliminated Spo11 activity of an endogenous Spo11 polynucleotide or polypeptide, wherein the Spo11 polynucleotide is selected from the group consisting of:
      i. a polynucleotide that encodes the polypeptide of SEQ ID NO:16;
      ii. a polynucleotide comprising the sequence set forth in SEQ ID NO:13, and
      iii. a polynucleotide having at least 95% sequence identity to SEQ ID NO: 13, wherein the Spo11 polypeptide is selected from the group consisting of:
         i. a polypeptide that is encoded by a nucleic acid molecule comprising a nucleotide sequence that is at least 95% identical to SEQ ID NO: 13, wherein the Spo11 activity of the endogenous Spo11 polynucleotide or polypeptide is eliminated by introducing a nucleotide modification into the Spo11 polynucleotide sequence or nucleic acid molecule in part a) to knock-out the endogenous Spo11 polynucleotide;
   b) eliminated Rec8 activity of an endogenous Rec8 polynucleotide or polypeptide, wherein Rec8 polynucleotide is selected from the group consisting of:
      i. a polynucleotide comprising the sequence set forth in SEQ ID NO:9; and
      ii. a polynucleotide having at least 95% sequence identity to SEQ ID NO: 9; wherein the Rec8 polypeptide is selected from the group consisting of:

i. a polypeptide that is encoded by a nucleic acid molecule comprising a nucleotide sequence that is at least 95% identical to SEQ ID NO:9, wherein the Rec8 activity of the endogenous Rec8 polynucleotide or polypeptide is eliminated by introducting a nucleotide modification into REC8 Polyculeotide sequence or nucleic acid molecule in part b) to knock-out the endogenour Rec8 polynucleotide;

c) eliminated OSD1-1A activity of an endogenous OSD1-1A poluynucleotide or polypeptide, wherein OSD1-1A polynuycleotide is selected from the group consisting of:
  i. a polynucleotide that encodes the polypeptide of SEQ ID NO:4;
  ii. a polynucleotide comprising the sequence set forth in SEQ ID NO:1; and
  iii. a polynucleotide having at least 95% sequence identitiy of SEQ ID NO:1; wherein the OSD1-1A polypeptide is selected form the group consisting of:
    i. a polypeptide that is encoded by a nucleic acid molecule comprising a nucleotide sequence that is at least 95% identical to SEQ ID NO:1,
  wherein the OSD1-1A activity of the endogenous OSD1-1A polynucleotide or polypeptide is eliminated by introducing a nucleotide modification into the OSD1-1A polynucleotide sequence or nucleic acid molecule in part c) to knock-out the endogenous OSD1-1A polynucleotide;
and d) eliminated OSD1-3A activity of an endogenous OSD1-3A polynucleotide or polypeptide, wherein OSD1-3A polynucleotide is selected from the group consisting of:
  i. a polynucleotide that encodes the polypeptide of SEQ ID NO:8;
  ii. a polynucleotide comprising the sequence set forth in SEQ ID NO:5; and
  iii. a polynucleotide having at least 95% sequence identity to SEQ ID NO:5; wherein the OSD1-3A polypeptide is selected form the group consisting of:
    i. a polypeptide that is encoded by a nucleic acid molecule comprising a nucleotide sequence that is at least 95% identical to SEQ ID NO: 5,
wherein the OSD1-3A activity of the endogenous OSD1-3A polynucleotide or polypeptide is eliminated by introducing a nucleotide modification into the OSD1-3A polynucleotide sequence of nucleic acid molecule in part d) to knock-out the endogenous OSD1-3A polynucleotide.

2. The maize plant of claim 1, wherein the maize plant is a hybrid.

3. The maize plant of claim 1, wherein the maize plant is a female parent.

4. The maize plant of claim 1, wherein the introduced nucleotide modification is a deletion, addition, or substitution of one or more nucleotides.

5. The maize plant of claim 1, wherein the introduced amino acid modification is a deletion, addition, or substitution of one or more amino acids.

6. The maize plant of claim 1, wherein said the nucleotide modification is introduced by a nuclease selected from the group consisting of: a TALEN, a meganuclease, a zinc finger nuclease, and a CRISPR-associated nuclease.

7. The maize plant of claim 6, wherein the nucleotide modification is introduced by a Cas9 endonuclease guided by at least one guide RNA.

8. A method for obtaining a maize plant producing clonal, non-reduced, non-recombined gametes, the method comprising:

a) eliminating in the maize plant the Spo11 activity of an endogenous Spo11 polynucleotide or polypeptide, wherein the Spo11 polynucleotide is selected from the group consisting of:
  i. a polynucleotide that encodes the polypeptide of SEQ ID NO:16;
  ii. a polynucleotide comprising the sequence set forth in SEQ ID NO:13; and
  iii. a polynucleotide having at least 95% sequence identity to SEQ ID NO: 13;
wherein the Spo11 polypeptide is selected from the group consisting of:
  i. a polypeptide that is encoded by a nucleic acid molecule comprising a nucleotide sequence that is at least 95% identical to SEQ ID NO:13;

b) eliminating in the maize plant the Rec8 activity of an endogenous Rec8 polynucleotide or polypeptide, wherein Rec8 polynucleotide is selected from the group consisting of:
  i. a polynucleotide comprising the sequence set forth in SEQ ID NO:9; and
  ii. a polynucleotide having at least 95% sequence identity to SEQ ID NO: 9;
wherein the Rec8 polypeptide is selected from the group consisting of:
  i. a polypeptide that is encoded by a nucleic acid molecule comprising a nucleotide sequence that is at least 95% identical to SEQ ID NO:9;

c) eliminating in the maize plant the OSD1-1A activity of an endogenous OSD1-1A polynucleotide or polypeptide, wherein OSD1-1A polynucleotide is selected from the group consisting of:
  i. a polynucleotide that encodes the polypeptide of SEQ ID NO:4;
  ii. a polynucleotide comprising the sequence set forth in SEQ ID NO:1; and
  iii. a polynucleotide having at least 95% sequence identity to SEQ ID NO: 1;
wherein the OSD1-1A polypeptide is selected from the group consisting of:
  i. a polypeptide that is encoded by a nucleic acid molecule comprising a nucleotide sequence that is at least 95% identical to SEQ ID NO:1; and d) eliminating in the maize plant the OSD1-3A activity of an endogenous OSD1-3A polynucleotide or polypeptide, wherein OSD1-3A polynucleotide is selected from the group consisting of:
  i. a polynucleotide that encodes the polypeptide of SEQ ID NO:8;
  ii. a polynucleotide comprising the sequence set forth in SEQ ID NO:5; and
  iii. a polynucleotide having at least 95% sequence identity to SEQ ID NO:5;
wherein the OSD1-3A polypeptide is selected from the group consisting of:
  i. a polypeptide that is encoded by a nucleic acid molecule comprising a nucleotide sequence that is at least 95% identical to SEQ ID NO: 5;
wherein the Spo11 activity of the endogenous Spo11 polynucleotide or polypeptide, wherein the Rec8 activity of the endogenous Rec8 polynucleotide or polypeptide, wherein the OSD1-1A activity of the endogenous OSD1-1A polynucleotide or polypeptide, wherein the OSD1-3A activity of the endogenous OSD1-3A polynucleotide or polypeptide, is eliminated by introducing a nucleotide modification into the polynucleotide sequence or nucleic acid molecule in part a), b), c), and d) respectively.

9. The method of claim 8, wherein the maize plant is a hybrid.

10. The method of claim 8, wherein the maize plant is a female parent.

11. The method of claim 8, wherein the nucleotide modification is a deletion, addition, or substitution of one or more nucleotides.

12. The method of claim 8, wherein the amino acid modification is a deletion, addition, or substitution of one or more amino acids.

13. The method of claim 11, wherein said the nucleotide modification is introduced by a nuclease selected from the group consisting of: a TALEN, a meganuclease, a zinc finger nuclease, and a CRISPR-associated nuclease.

14. The method of claim 13, wherein the nucleotide modification is introduced by a Cas9 endonuclease guided by at least one guide RNA.

15. The method of claim 8, wherein the maize plant is obtained by crossing maize plants that are heterozygous or homozygous for the eliminated endogenous Spo11, Rec8, OSD1-1A or OSD1-3A activity.

16. The method of claim 8, further comprising obtaining gametes from the female parent, wherein the gametes are clonal, non-reduced, non-recombined.

17. Clonal, non-reduced, non-recombined gametes obtained from the method of claim 8, wherein the introduced nucleotide modifications into the Spo11, Rec8, OSD1-1A, and OSD1-3A polynucleotide sequences in the maize plant render the gametes clonal, non-reduced, and non-recombined.

18. A maize plant comprising clonal, non-reduced, non-recombined gametes produced from the method of claim 8.

19. The maize plant of claim 1, wherein the nucleotide modification is introduced by chemical mutagenesis.

20. The method of claim 8, wherein the nucleotide modification is introduced by chemical mutagenesis.

* * * * *